(12) United States Patent
Conklin et al.

(10) Patent No.: US 6,380,361 B1
(45) Date of Patent: Apr. 30, 2002

(54) EDUCATIONAL KIT AND METHOD CONTAINING NOVEL ALPHA HELICAL PROTEIN-34

(75) Inventors: Darrell C. Conklin; David W. Taft, both of Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/695,458

(22) Filed: Oct. 24, 2000

Related U.S. Application Data

(60) Provisional application No. 60/162,623, filed on Oct. 29, 1999.

(51) Int. Cl.$^7$ ................................................. C12Q 1/68
(52) U.S. Cl. .......................... 530/350; 536/23.5; 435/6; 435/320.1
(58) Field of Search ............................... 530/350; 435/6, 435/320.1; 536/23.5

(56) References Cited

U.S. PATENT DOCUMENTS 6,303,770 B1 * 10/2001 Lok et al. ................... 536/23.5

OTHER PUBLICATIONS

GenBank Accession No. AA066036, Sep. 23, 1996.
Sequence for Incyte Pharmaceuticals, Inc., INC1973483, Nov. 5, 1996.
Sequence for Incyte Pharmaceuticals, Inc., INC1259269, May. 20, 1996.
Sequence for Incyte Pharmaceuticals, Inc., INC3417089, Sep. 8, 1997.
GenBank Accession No. AA718937, Dec. 24, 1997.
GenBank Accession No. AA682767, Dec. 24, 1997.
Sequence for Incyte Pharmaceuticals, Inc., INC4255283, Feb. 9, 1998.
Sequence for Incyte Pharmaceuticals, Inc., INC4770471, Apr. 10, 1998.
Sequence for Incyte Pharmaceuticals, Inc., INC584555, Apr. 7, 1999.
Sequence for Incyte Pharmaceuticals, Inc., INC5848523, Apr. 7, 1999.
GenBank Accession No. AI595527, Apr. 12, 1999.
GenBank Accession No. AI429177, Feb. 10, 1999.
GenBank Accession No. AI595527, Apr. 12, 1999.
GenBank Accession No. AV042148, May. 18, 1999.
GenBank Accession No. AV040612, May. 18, 1999.
GenBank Accession No. AV041832, May. 18, 1999.
GenBank Accession No. AV044010, May. 18, 1999.
GenBank Accession No. AV040479, May. 18, 1999.
GenBank Accession No. AV260148, Nov. 4, 1999.
GenBank Accession No. AV257441, Nov. 4, 1999.
GenBank Accession No. AV257758, Nov. 4, 1999.
GenBank Accession No. AV256899, Nov. 4, 1999.
GenBank Accession No. AV259567, Nov. 4, 1999.
GenBank Accession No. AV262363, Nov. 5, 1999.
GenBank Accession No. AV268647, Nov. 5, 1999.
GenBank Accession No. AV270567, Nov. 5, 1999.
GenBank Accession No. AV281185, Nov. 5, 1999.
GenBank Accession No. AV279243, Nov. 5, 1999.
GenBank Accession No. AV279078, Nov. 5, 1999.
GenBank Accession No. AV265958, Nov. 5, 1999.
GenBank Accession No. AV281853, Nov. 5, 1999.
GenBank Accession No. AV278985, Nov. 5, 1999.

\* cited by examiner

*Primary Examiner*—W. Gary Jones
*Assistant Examiner*—Janell E. Taylor
(74) *Attorney, Agent, or Firm*—Paul G. Lunn, Esq.

(57) ABSTRACT

An educational kit comprised of novel a novel polypeptide, alpha helical protein-34 (Zalpha34), polynucleotides that encode Zalpha34 and antibodies to Zalpha34. The present invention also relates to polynucleotide and polypeptide molecules for Zalpha34. The polypeptides, and polynucleotides encoding them, are hormonal and may be used to promote spermatogenesis. The present invention also includes antibodies to the Zalpha34 polypeptides, which can be used to inhibit spermatogenesis.

3 Claims, No Drawings

SEQUENCE LISTING

```
<160> NUMBER OF SEQ ID NOS: 41

<210> SEQ ID NO 1
<211> LENGTH: 1449
<212> TYPE: DNA
<213> ORGANISM: Mus musculis
<220> FEATURE:
<221> NAME/KEY: CDS
<222> LOCATION: (22)...(1014)

<400> SEQUENCE: 1
cagctgagga agtggagcag t atg gcc acc aga ccg cag ccg ttg ggt atg         51
              Met Ala Thr Arg Pro Gln Pro Leu Gly Met
                1               5                  10 gag ccc gag ggc tca gca gac ctg ctc cac ggg cct gag ggg gcc aga         99
Glu Pro Glu Gly Ser Ala Asp Leu Leu His Gly Pro Glu Gly Ala Arg
                15                  20                  25 ggg cag tat ggg tcc aca cag aaa att gaa gac tta atg gac atg gtg        147
Gly Gln Tyr Gly Ser Thr Gln Lys Ile Glu Asp Leu Met Asp Met Val
            30                  35                  40 aaa aag ttg cag aaa gtg gga agc cta gag ccc cgg att gag gtc ctg        195
Lys Lys Leu Gln Lys Val Gly Ser Leu Glu Pro Arg Ile Glu Val Leu
        45                  50                  55 att aac cgt att aat gag gtt cag caa ggt aaa gca aaa aag aaa gcc        243
Ile Asn Arg Ile Asn Glu Val Gln Gln Gly Lys Ala Lys Lys Lys Ala
```

-continued

| | | |
|---|---|---|
| agt gag gag ctt gga gag gcc cag act gtc tgg gac aac ctg cag aag<br>Ser Glu Glu Leu Gly Glu Ala Gln Thr Val Trp Asp Asn Leu Gln Lys<br>75                        80                        85                        90 | 291 |
| gaa ctg gac tta cta cgt gaa gag aaa gta cgt ctg aag gat att ttg<br>Glu Leu Asp Leu Leu Arg Glu Glu Lys Val Arg Leu Lys Asp Ile Leu<br>                        95                        100                      105 | 339 |
| aac aga aag gaa gag acc ctg agg att atg cag ctg cac tgc cag gag<br>Asn Arg Lys Glu Glu Thr Leu Arg Ile Met Gln Leu His Cys Gln Glu<br>                        110                      115                      120 | 387 |
| aag gaa agt gag gca cag agg aag cac agc atg ttg cag gag tgt aaa<br>Lys Glu Ser Glu Ala Gln Arg Lys His Ser Met Leu Gln Glu Cys Lys<br>              125                      130                      135 | 435 |
| gag aga att tct ttc ctg aac tcc cag atc gac aaa gag aag gcc aaa<br>Glu Arg Ile Ser Phe Leu Asn Ser Gln Ile Asp Lys Glu Lys Ala Lys<br>    140                      145                      150 | 483 |
| cta aga aaa ctg agg ttg gat ttt gaa gaa cat ctg gag act ttg atg<br>Leu Arg Lys Leu Arg Leu Asp Phe Glu Glu His Leu Glu Thr Leu Met<br>155                        160                      165                      170 | 531 |
| agt caa cat aag gac acc ttg gaa ttt cat aag cct gaa cat ctg aca<br>Ser Gln His Lys Asp Thr Leu Glu Phe His Lys Pro Glu His Leu Thr<br>              175                      180                      185 | 579 |
| aag gag atg tgt gtt ttg gac agc agc aag gag cag ctg ctc aag gaa<br>Lys Glu Met Cys Val Leu Asp Ser Ser Lys Glu Gln Leu Leu Lys Glu<br>                  190                      195                      200 | 627 |
| gag aaa ctg atg aaa gta aag ctg gag gat gtg aga cag cgg ctg tgt<br>Glu Lys Leu Met Lys Val Lys Leu Glu Asp Val Arg Gln Arg Leu Cys<br>              205                      210                      215 | 675 |
| gcc ctg ggc ggg cct gag ggt tct tcc agc ctc att gag gga ctc ttc<br>Ala Leu Gly Gly Pro Glu Gly Ser Ser Ser Leu Ile Glu Gly Leu Phe<br>220                        225                      230 | 723 |
| ctc cga agc cat gag gca gct gca gca atg cag atg ttc aag gat gag<br>Leu Arg Ser His Glu Ala Ala Ala Ala Met Gln Met Phe Lys Asp Glu<br>235                        240                      245                      250 | 771 |
| aac aag aaa gct gag gag ttc cta gag gct gca gct cag cag cac gag<br>Asn Lys Lys Ala Glu Glu Phe Leu Glu Ala Ala Ala Gln Gln His Glu<br>                  255                      260                      265 | 819 |
| cag ctg cag cag agg tgc cac cag cta cag cag aaa cgg cag agg ctg<br>Gln Leu Gln Gln Arg Cys His Gln Leu Gln Gln Lys Arg Gln Arg Leu<br>              270                      275                      280 | 867 |
| aag gaa gaa ctg gaa aag cat ggg gta cag atc ctt gct cat agt acg<br>Lys Glu Glu Leu Glu Lys His Gly Val Gln Ile Leu Ala His Ser Thr<br>    285                      290                      295 | 915 |
| caa aac gaa gaa gac agc tca tgg agg atg gcc agt cct aaa cct gta<br>Gln Asn Glu Glu Asp Ser Ser Trp Arg Met Ala Ser Pro Lys Pro Val<br>300                        305                      310 | 963 |
| gaa gtc cac gag gag aca gcc caa gac caa gag cgc cca tca agc agg<br>Glu Val His Glu Glu Thr Ala Gln Asp Gln Glu Arg Pro Ser Ser Arg<br>315                        320                      325                      330 | 1011 |
| acc taatccctc ctcagcctgg aggacttact gacttcagac atcacttgcg<br>Thr | 1064 |
| gatgttttgt gtagcctgct tcatctgagt atgtgccgag tggaagaatg ggtgttgggg | 1124 |
| ccaagcccct caagtctttg aacctggaga tgtcttggct caattttgag tttcacctag | 1184 |
| cttagggtcc acactgcaga cccttagtaa atgctttccc tgtctcttgc tcaccactag | 1244 |
| tatctgacac acgcttcttc tcttgagcag aggatgctga tctgaacctt ctcacaggat | 1304 |
| ctgaagccac ttggtaattt agttccctca tgtaggccca gaatagcata tactttgaaa | 1364 |

```
caaaaggaag acacatcacc agctcttaat tctcactata aaccacctca ttcttcaagc   1424
aaaataaatg aaatttaagt ctgca                                         1449
```

<210> SEQ ID NO 2
<211> LENGTH: 331
<212> TYPE: PRT
<213> ORGANISM: Mus musculis

<400> SEQUENCE: 2

```
Met Ala Thr Arg Pro Gln Pro Leu Gly Met Glu Pro Glu Gly Ser Ala
 1               5                  10                  15

Asp Leu Leu His Gly Pro Glu Gly Ala Arg Gly Gln Tyr Gly Ser Thr
            20                  25                  30

Gln Lys Ile Glu Asp Leu Met Asp Met Val Lys Lys Leu Gln Lys Val
        35                  40                  45

Gly Ser Leu Glu Pro Arg Ile Glu Val Leu Ile Asn Arg Ile Asn Glu
    50                  55                  60

Val Gln Gln Gly Lys Ala Lys Lys Ala Ser Glu Glu Leu Gly Glu
65                  70                  75                  80

Ala Gln Thr Val Trp Asp Asn Leu Gln Lys Glu Leu Asp Leu Leu Arg
                85                  90                  95

Glu Glu Lys Val Arg Leu Lys Asp Ile Leu Asn Arg Lys Glu Glu Thr
            100                 105                 110

Leu Arg Ile Met Gln Leu His Cys Gln Glu Lys Glu Ser Glu Ala Gln
        115                 120                 125

Arg Lys His Ser Met Leu Gln Glu Cys Lys Glu Arg Ile Ser Phe Leu
    130                 135                 140

Asn Ser Gln Ile Asp Lys Glu Lys Ala Lys Leu Arg Lys Leu Arg Leu
145                 150                 155                 160

Asp Phe Glu Glu His Leu Glu Thr Leu Met Ser Gln His Lys Asp Thr
                165                 170                 175

Leu Glu Phe His Lys Pro Glu His Leu Thr Lys Glu Met Cys Val Leu
            180                 185                 190

Asp Ser Ser Lys Glu Gln Leu Leu Lys Glu Lys Leu Met Lys Val
        195                 200                 205

Lys Leu Glu Asp Val Arg Gln Arg Leu Cys Ala Leu Gly Gly Pro Glu
    210                 215                 220

Gly Ser Ser Ser Leu Ile Glu Gly Leu Phe Leu Arg Ser His Glu Ala
225                 230                 235                 240

Ala Ala Ala Met Gln Met Phe Lys Asp Glu Asn Lys Lys Ala Glu Glu
                245                 250                 255

Phe Leu Glu Ala Ala Gln His Glu Gln Leu Gln Gln Arg Cys
            260                 265                 270

His Gln Leu Gln Lys Arg Gln Arg Leu Lys Glu Glu Leu Glu Lys
        275                 280                 285

His Gly Val Gln Ile Leu Ala His Ser Thr Gln Asn Glu Glu Asp Ser
    290                 295                 300

Ser Trp Arg Met Ala Ser Pro Lys Pro Val Glu Val His Glu Glu Thr
305                 310                 315                 320

Ala Gln Asp Gln Glu Arg Pro Ser Ser Arg Thr
                325                 330
```

<210> SEQ ID NO 3
<211> LENGTH: 304
<212> TYPE: PRT

```
<213> ORGANISM: Mus musculis

<400> SEQUENCE: 3

Gln Tyr Gly Ser Thr Gln Lys Ile Glu Asp Leu Met Asp Met Val Lys
 1               5                  10                  15

Lys Leu Gln Lys Val Gly Ser Leu Glu Pro Arg Ile Glu Val Leu Ile
             20                  25                  30

Asn Arg Ile Asn Glu Val Gln Gln Gly Lys Ala Lys Lys Lys Ala Ser
         35                  40                  45

Glu Glu Leu Gly Glu Ala Gln Thr Val Trp Asp Asn Leu Gln Lys Glu
     50                  55                  60

Leu Asp Leu Leu Arg Glu Glu Lys Val Arg Leu Lys Asp Ile Leu Asn
 65                  70                  75                  80

Arg Lys Glu Glu Thr Leu Arg Ile Met Gln Leu His Cys Gln Glu Lys
                 85                  90                  95

Glu Ser Glu Ala Gln Arg Lys His Ser Met Leu Gln Glu Cys Lys Glu
            100                 105                 110

Arg Ile Ser Phe Leu Asn Ser Gln Ile Asp Lys Glu Lys Ala Lys Leu
        115                 120                 125

Arg Lys Leu Arg Leu Asp Phe Glu Glu His Leu Glu Thr Leu Met Ser
    130                 135                 140

Gln His Lys Asp Thr Leu Glu Phe His Lys Pro Glu His Leu Thr Lys
145                 150                 155                 160

Glu Met Cys Val Leu Asp Ser Ser Lys Glu Gln Leu Leu Lys Glu Glu
                165                 170                 175

Lys Leu Met Lys Val Lys Leu Glu Asp Val Arg Gln Arg Leu Cys Ala
            180                 185                 190

Leu Gly Gly Pro Glu Gly Ser Ser Leu Ile Glu Gly Leu Phe Leu
        195                 200                 205

Arg Ser His Glu Ala Ala Ala Met Gln Met Phe Lys Asp Glu Asn
    210                 215                 220

Lys Lys Ala Glu Glu Phe Leu Glu Ala Ala Gln Gln His Glu Gln
225                 230                 235                 240

Leu Gln Gln Arg Cys His Gln Leu Gln Gln Lys Arg Gln Arg Leu Lys
                245                 250                 255

Glu Glu Leu Glu Lys His Gly Val Gln Ile Leu Ala His Ser Thr Gln
            260                 265                 270

Asn Glu Glu Asp Ser Ser Trp Arg Met Ala Ser Pro Lys Pro Val Glu
        275                 280                 285

Val His Glu Glu Thr Ala Gln Asp Gln Glu Arg Pro Ser Ser Arg Thr
    290                 295                 300

<210> SEQ ID NO 4
<211> LENGTH: 15
<212> TYPE: PRT
<213> ORGANISM: Mus musculis

<400> SEQUENCE: 4

Tyr Gly Ser Thr Gln Lys Ile Glu Asp Leu Met Asp Met Val Lys
 1               5                  10                  15

<210> SEQ ID NO 5
<211> LENGTH: 15
<212> TYPE: PRT
<213> ORGANISM: Mus musculis

<400> SEQUENCE: 5
```

```
Glu Leu Gly Glu Ala Gln Thr Val Trp Asp Asn Leu Gln Lys Glu
1               5                   10                  15

<210> SEQ ID NO 6
<211> LENGTH: 15
<212> TYPE: PRT
<213> ORGANISM: Mus musculis

<400> SEQUENCE: 6

Glu Lys Val Arg Leu Lys Asp Ile Leu Asn Arg Lys Glu Glu Thr
1               5                   10                  15

<210> SEQ ID NO 7
<211> LENGTH: 15
<212> TYPE: PRT
<213> ORGANISM: Mus musculis

<400> SEQUENCE: 7

Lys His Ser Met Leu Gln Glu Cys Lys Glu Arg Ile Ser Phe Leu
1               5                   10                  15

<210> SEQ ID NO 8
<211> LENGTH: 29
<212> TYPE: PRT
<213> ORGANISM: Mus musculis

<400> SEQUENCE: 8

Gln Tyr Gly Ser Thr Gln Lys Ile Glu Asp Leu Met Asp Met Val Lys
1               5                   10                  15

Lys Leu Gln Lys Val Gly Ser Leu Glu Pro Arg Ile Glu
            20                  25

<210> SEQ ID NO 9
<211> LENGTH: 50
<212> TYPE: PRT
<213> ORGANISM: Mus musculis

<400> SEQUENCE: 9

Asn Glu Val Gln Gln Gly Lys Ala Lys Lys Ala Ser Glu Glu Leu
1               5                   10                  15

Gly Glu Ala Gln Thr Val Trp Asp Asn Leu Gln Lys Glu Leu Asp Leu
                20                  25                  30

Leu Arg Glu Glu Lys Val Arg Leu Lys Asp Ile Leu Asn Arg Lys Glu
        35                  40                  45

Glu Thr
    50

<210> SEQ ID NO 10
<211> LENGTH: 44
<212> TYPE: PRT
<213> ORGANISM: Mus musculis

<400> SEQUENCE: 10

Gln Glu Lys Glu Ser Glu Ala Gln Arg Lys His Ser Met Leu Gln Glu
1               5                   10                  15

Cys Lys Glu Arg Ile Ser Phe Leu Asn Ser Gln Ile Asp Lys Glu Lys
                20                  25                  30

Ala Lys Leu Arg Lys Leu Arg Leu Asp Phe Glu Glu
        35                  40

<210> SEQ ID NO 11
```

```
<211> LENGTH: 44
<212> TYPE: PRT
<213> ORGANISM: Mus musculis

<400> SEQUENCE: 11

His Lys Asp Thr Leu Glu Phe His Lys Pro Glu His Leu Thr Lys Glu
 1               5                   10                  15

Met Cys Val Leu Asp Ser Ser Lys Glu Gln Leu Leu Lys Glu Glu Lys
                20                  25                  30

Leu Met Lys Val Lys Leu Glu Asp Val Arg Gln Arg
            35                  40

<210> SEQ ID NO 12
<211> LENGTH: 67
<212> TYPE: PRT
<213> ORGANISM: Mus musculis

<400> SEQUENCE: 12

Gly Pro Glu Gly Ser Ser Ser Leu Ile Glu Gly Leu Phe Leu Arg Ser
 1               5                   10                  15

His Glu Ala Ala Ala Met Gln Met Phe Lys Asp Glu Asn Lys Lys
                20                  25                  30

Ala Glu Glu Phe Leu Glu Ala Ala Gln Gln His Glu Gln Leu Gln
            35                  40                  45

Gln Arg Cys His Gln Leu Gln Gln Lys Arg Gln Arg Leu Lys Glu Glu
        50                  55                  60

Leu Glu Lys
65

<210> SEQ ID NO 13
<211> LENGTH: 35
<212> TYPE: PRT
<213> ORGANISM: Mus musculis

<400> SEQUENCE: 13

Ser Thr Gln Asn Glu Glu Asp Ser Ser Trp Arg Met Ala Ser Pro Lys
 1               5                   10                  15

Pro Val Glu Val His Glu Glu Thr Ala Gln Asp Gln Glu Arg Pro Ser
                20                  25                  30

Ser Arg Thr
        35

<210> SEQ ID NO 14
<211> LENGTH: 42
<212> TYPE: PRT
<213> ORGANISM: Mus musculis

<400> SEQUENCE: 14

Gly Ser Thr Gln Lys Ile Glu Asp Leu Met Asp Met Val Lys Lys Leu
 1               5                   10                  15

Gln Lys Val Gly Ser Leu Glu Pro Arg Ile Glu Val Leu Ile Asn Arg
                20                  25                  30

Ile Asn Glu Val Gln Gln Gly Lys Ala Lys
            35                  40

<210> SEQ ID NO 15
<211> LENGTH: 37
<212> TYPE: PRT
<213> ORGANISM: Mus musculis

<400> SEQUENCE: 15
```

```
Glu Glu Leu Gly Glu Ala Gln Thr Val Trp Asp Asn Leu Gln Lys Glu
 1               5                   10                  15

Leu Asp Leu Leu Arg Glu Glu Lys Val Arg Leu Lys Asp Ile Leu Asn
                20                  25                  30

Arg Lys Glu Glu Thr
            35
```

<210> SEQ ID NO 16
<211> LENGTH: 47
<212> TYPE: PRT
<213> ORGANISM: Mus musculis

<400> SEQUENCE: 16

```
Lys His Ser Met Leu Gln Glu Cys Lys Glu Arg Ile Ser Phe Leu Asn
 1               5                   10                  15

Ser Gln Ile Asp Lys Glu Lys Ala Lys Leu Arg Lys Leu Arg Leu Asp
                20                  25                  30

Phe Glu Glu His Leu Glu Thr Leu Met Ser Gln His Lys Asp Thr
            35                  40                  45
```

<210> SEQ ID NO 17
<211> LENGTH: 36
<212> TYPE: PRT
<213> ORGANISM: Mus musculis

<400> SEQUENCE: 17

```
Asp Ser Ser Lys Glu Gln Leu Leu Lys Glu Glu Lys Leu Met Lys Val
 1               5                   10                  15

Lys Leu Glu Asp Val Arg Gln Arg Leu Cys Ala Leu Gly Gly Pro Glu
                20                  25                  30

Gly Ser Ser Ser
            35
```

<210> SEQ ID NO 18
<211> LENGTH: 76
<212> TYPE: PRT
<213> ORGANISM: Mus musculis

<400> SEQUENCE: 18

```
Asp Glu Asn Lys Lys Ala Glu Glu Phe Leu Glu Ala Ala Ala Gln Gln
 1               5                   10                  15

His Glu Gln Leu Gln Gln Arg Cys His Gln Leu Gln Gln Lys Arg Gln
                20                  25                  30

Arg Leu Lys Glu Glu Leu Glu Lys His Gly Val Gln Ile Leu Ala His
            35                  40                  45

Ser Thr Gln Asn Glu Glu Asp Ser Ser Trp Arg Met Ala Ser Pro Lys
        50                  55                  60

Pro Val Glu Val His Glu Glu Thr Ala Gln Asp Gln
65                  70                  75
```

<210> SEQ ID NO 19
<211> LENGTH: 26
<212> TYPE: PRT
<213> ORGANISM: Mus musculis

<400> SEQUENCE: 19

```
Ser Ser Trp Arg Met Ala Ser Pro Lys Pro Val Glu Val His Glu Glu
 1               5                   10                  15

Thr Ala Gln Asp Gln Glu Arg Pro Ser Ser
                20                  25
```

<210> SEQ ID NO 20
<211> LENGTH: 23
<212> TYPE: PRT
<213> ORGANISM: Mus musculis

<400> SEQUENCE: 20

```
Thr Gln Asn Glu Glu Asp Ser Ser Trp Arg Met Ala Ser Pro Lys Pro
1               5                   10                  15

Val Glu Val His Glu Glu Thr
            20
```

<210> SEQ ID NO 21
<211> LENGTH: 1381
<212> TYPE: DNA
<213> ORGANISM: Homo sapiens
<220> FEATURE:
<221> NAME/KEY: CDS
<222> LOCATION: (70)...(1023)

<400> SEQUENCE: 21

| | | |
|---|---|---:|
| agcggcggtt gctccaatca ccactggagg ctccctcccg aggcaccctc gctggcgagc | | 60 |

| | | | | | | | | | | | | | | | | |
|---|---|---|---|---|---|---|---|---|---|---|---|---|---|---|---|---:|
| tgagaggaa | atg | gcg | ggg | agg | tcc | ctg | aca | tcg | aag | gcc | gag | ccc | acc | gca | | 111 |
| | Met | Ala | Gly | Arg | Ser | Leu | Thr | Ser | Lys | Ala | Glu | Pro | Thr | Ala | | |
| | 1 | | | | 5 | | | | | 10 | | | | | | |
| gga | gcc | gtg | gac | agg | gct | gag | aag | gcc | gga | ggg | cag | gac | acg | tcc | tca | 159 |
| Gly | Ala | Val | Asp | Arg | Ala | Glu | Lys | Ala | Gly | Gly | Gln | Asp | Thr | Ser | Ser | |
| 15 | | | | 20 | | | | | 25 | | | | | 30 | | |
| cag | aaa | att | gaa | gac | ttg | atg | gaa | atg | gtg | caa | aag | ctg | cag | aaa | gtg | 207 |
| Gln | Lys | Ile | Glu | Asp | Leu | Met | Glu | Met | Val | Gln | Lys | Leu | Gln | Lys | Val | |
| | | | 35 | | | | | 40 | | | | | 45 | | | |
| gga | agc | cta | gag | ccc | cga | gtt | gag | gtc | ctg | att | aac | cgg | att | aat | gag | 255 |
| Gly | Ser | Leu | Glu | Pro | Arg | Val | Glu | Val | Leu | Ile | Asn | Arg | Ile | Asn | Glu | |
| | | 50 | | | | | 55 | | | | | 60 | | | | |
| gtc | cag | caa | gca | aaa | aag | aaa | gcc | aat | aaa | gac | cta | gga | gag | gcc | cgg | 303 |
| Val | Gln | Gln | Ala | Lys | Lys | Lys | Ala | Asn | Lys | Asp | Leu | Gly | Glu | Ala | Arg | |
| | 65 | | | | | 70 | | | | | 75 | | | | | |
| acc | atc | tgt | gag | gcc | ctg | cag | aag | gaa | ctg | gac | tcg | ctg | cat | gga | gag | 351 |
| Thr | Ile | Cys | Glu | Ala | Leu | Gln | Lys | Glu | Leu | Asp | Ser | Leu | His | Gly | Glu | |
| | 80 | | | | | 85 | | | | | 90 | | | | | |
| aaa | gta | cac | ctg | aag | gag | atc | ttg | agc | aaa | aaa | caa | gag | acc | ctg | agg | 399 |
| Lys | Val | His | Leu | Lys | Glu | Ile | Leu | Ser | Lys | Lys | Gln | Glu | Thr | Leu | Arg | |
| 95 | | | | | 100 | | | | | 105 | | | | | 110 | |
| atc | ctc | cgg | ctg | cat | tgc | cag | gaa | aag | gaa | agt | gag | gca | cac | agg | aag | 447 |
| Ile | Leu | Arg | Leu | His | Cys | Gln | Glu | Lys | Glu | Ser | Glu | Ala | His | Arg | Lys | |
| | | | | 115 | | | | | 120 | | | | | 125 | | |
| cac | acc | atg | ttg | cag | gag | tgc | aag | gag | aga | att | tct | gcc | ctg | aac | ttg | 495 |
| His | Thr | Met | Leu | Gln | Glu | Cys | Lys | Glu | Arg | Ile | Ser | Ala | Leu | Asn | Leu | |
| | | | 130 | | | | | 135 | | | | | 140 | | | |
| cag | att | gaa | gaa | gag | aag | aac | aaa | cag | aga | cag | ctg | agg | ttg | gca | ttc | 543 |
| Gln | Ile | Glu | Glu | Glu | Lys | Asn | Lys | Gln | Arg | Gln | Leu | Arg | Leu | Ala | Phe | |
| | | 145 | | | | | 150 | | | | | 155 | | | | |
| gag | gaa | cag | ctg | gaa | gat | ctg | atg | ggc | cag | cac | aag | gac | ctc | tgg | gac | 591 |
| Glu | Glu | Gln | Leu | Glu | Asp | Leu | Met | Gly | Gln | His | Lys | Asp | Leu | Trp | Asp | |
| | 160 | | | | | 165 | | | | | 170 | | | | | |
| ttc | cac | atg | cca | gag | cgg | ctg | gca | aag | gag | att | tgt | gcc | ctg | gac | agc | 639 |
| Phe | His | Met | Pro | Glu | Arg | Leu | Ala | Lys | Glu | Ile | Cys | Ala | Leu | Asp | Ser | |
| 175 | | | | | 180 | | | | | 185 | | | | | 190 | |
| agc | aag | gag | cag | ctg | ctc | aag | gaa | gag | aag | ctg | gtc | aag | gcg | aca | ctg | 687 |
| Ser | Lys | Glu | Gln | Leu | Leu | Lys | Glu | Glu | Lys | Leu | Val | Lys | Ala | Thr | Leu | |

-continued

```
                        195                 200                 205
gaa gac gtg aag cat cag ctg tgc tcc ctg tgt ggg gct gag ggc ccc      735
Glu Asp Val Lys His Gln Leu Cys Ser Leu Cys Gly Ala Glu Gly Pro
            210                 215                 220 tcc acc ctt gat gag gga ctc ttt ctc cgc agc cag gag gct gca gcc      783
Ser Thr Leu Asp Glu Gly Leu Phe Leu Arg Ser Gln Glu Ala Ala Ala
        225                 230                 235 aca gtg cag ctg ttt cag gaa gag cac agg aag gct gag gag ctc cta      831
Thr Val Gln Leu Phe Gln Glu Glu His Arg Lys Ala Glu Glu Leu Leu
    240                 245                 250 gca gct gct gcc cag cgc cac cag cag ctg cag cag aag tgc caa caa      879
Ala Ala Ala Ala Gln Arg His Gln Gln Leu Gln Gln Lys Cys Gln Gln
255                 260                 265                 270 cag cag cag aag cgg cag agg ctg aag gaa gag ctg gaa aag cat gga      927
Gln Gln Gln Lys Arg Gln Arg Leu Lys Glu Glu Leu Glu Lys His Gly
                275                 280                 285 atg caa gtc cct gcc caa gcc cag agc aca caa gag gaa gag gct ggc      975
Met Gln Val Pro Ala Gln Ala Gln Ser Thr Gln Glu Glu Glu Ala Gly
            290                 295                 300 cca gga gat gtg gct ccc aga cca ggt aga cca gtg aca tgg tgg agt     1023
Pro Gly Asp Val Ala Pro Arg Pro Gly Arg Pro Val Thr Trp Trp Ser
        305                 310                 315 tgaagagaga ggctcactgc agagcactgt ttccatggaa aaatgaaaca tggcaaagtg    1083
cagaaattct tcagtcagtc caggacagac gagttctcta agatgcagtt aatcatacct    1143
gtcttaaaca aactggcaat atactatcaa acatgacttt taaatcaagt ggaagttaga    1203
aaatatattg aactgagtgg caatgaagac accacatttt aaaactgtaa ttcagttaag    1263
cccacaatta gaaggaactt tagctttat tggttcacca caattttta agaaatcaac     1323 caatgattgt tcagttaatg aataaaaggc ctttgacaca gttcacctat tcatgtga      1381
```

<210> SEQ ID NO 22
<211> LENGTH: 318
<212> TYPE: PRT
<213> ORGANISM: Homo sapiens

<400> SEQUENCE: 22

```
Met Ala Gly Arg Ser Leu Thr Ser Lys Ala Glu Pro Thr Ala Gly Ala
 1               5                  10                  15

Val Asp Arg Ala Glu Lys Ala Gly Gly Gln Asp Thr Ser Ser Gln Lys
            20                  25                  30

Ile Glu Asp Leu Met Glu Met Val Gln Lys Leu Gln Lys Val Gly Ser
        35                  40                  45

Leu Glu Pro Arg Val Glu Val Leu Ile Asn Arg Ile Asn Glu Val Gln
    50                  55                  60

Gln Ala Lys Lys Lys Ala Asn Lys Asp Leu Gly Glu Ala Arg Thr Ile
65                  70                  75                  80

Cys Glu Ala Leu Gln Lys Glu Leu Asp Ser Leu His Gly Glu Lys Val
                85                  90                  95

His Leu Lys Glu Ile Leu Ser Lys Gln Glu Thr Leu Arg Ile Leu
            100                 105                 110

Arg Leu His Cys Gln Glu Lys Glu Ser Glu Ala His Arg Lys His Thr
        115                 120                 125

Met Leu Gln Glu Cys Lys Glu Arg Ile Ser Ala Leu Asn Leu Gln Ile
    130                 135                 140

Glu Glu Glu Lys Asn Lys Gln Arg Gln Leu Arg Leu Ala Phe Glu Glu
145                 150                 155                 160
```

-continued

```
Gln Leu Glu Asp Leu Met Gly Gln His Lys Asp Leu Trp Asp Phe His
                165                 170                 175
Met Pro Glu Arg Leu Ala Lys Glu Ile Cys Ala Leu Asp Ser Ser Lys
            180                 185                 190
Glu Gln Leu Leu Lys Glu Lys Leu Val Lys Ala Thr Leu Glu Asp
        195                 200                 205
Val Lys His Gln Leu Cys Ser Leu Cys Gly Ala Glu Gly Pro Ser Thr
    210                 215                 220
Leu Asp Glu Gly Leu Phe Leu Arg Ser Gln Glu Ala Ala Thr Val
225                 230                 235                 240
Gln Leu Phe Gln Glu Glu His Arg Lys Ala Glu Glu Leu Leu Ala Ala
                245                 250                 255
Ala Ala Gln Arg His Gln Gln Leu Gln Gln Lys Cys Gln Gln Gln Gln
            260                 265                 270
Gln Lys Arg Gln Arg Leu Lys Glu Glu Leu Glu Lys His Gly Met Gln
        275                 280                 285
Val Pro Ala Gln Ala Gln Ser Thr Gln Glu Glu Ala Gly Pro Gly
    290                 295                 300
Asp Val Ala Pro Arg Pro Gly Arg Pro Val Thr Trp Trp Ser
305                 310                 315
```

<210> SEQ ID NO 23
<211> LENGTH: 293
<212> TYPE: PRT
<213> ORGANISM: Homo sapiens

<400> SEQUENCE: 23

```
Gln Asp Thr Ser Ser Gln Lys Ile Glu Asp Leu Met Glu Met Val Gln
  1               5                  10                  15
Lys Leu Gln Lys Val Gly Ser Leu Glu Pro Arg Val Glu Val Leu Ile
            20                  25                  30
Asn Arg Ile Asn Glu Val Gln Gln Ala Lys Lys Lys Ala Asn Lys Asp
        35                  40                  45
Leu Gly Glu Ala Arg Thr Ile Cys Glu Ala Leu Gln Lys Glu Leu Asp
    50                  55                  60
Ser Leu His Gly Glu Lys Val His Leu Lys Glu Ile Leu Ser Lys Lys
65                  70                  75                  80
Gln Glu Thr Leu Arg Ile Leu Arg Leu His Cys Gln Glu Lys Glu Ser
                85                  90                  95
Glu Ala His Arg Lys His Thr Met Leu Gln Glu Cys Lys Glu Arg Ile
            100                 105                 110
Ser Ala Leu Asn Leu Gln Ile Glu Glu Glu Lys Asn Lys Gln Arg Gln
        115                 120                 125
Leu Arg Leu Ala Phe Glu Glu Gln Leu Glu Asp Leu Met Gly Gln His
    130                 135                 140
Lys Asp Leu Trp Asp Phe His Met Pro Glu Arg Leu Ala Lys Glu Ile
145                 150                 155                 160
Cys Ala Leu Asp Ser Ser Lys Glu Gln Leu Leu Lys Glu Lys Leu
                165                 170                 175
Val Lys Ala Thr Leu Glu Asp Val Lys His Gln Leu Cys Ser Leu Cys
            180                 185                 190
Gly Ala Glu Gly Pro Ser Thr Leu Asp Glu Gly Leu Phe Leu Arg Ser
        195                 200                 205
Gln Glu Ala Ala Ala Thr Val Gln Leu Phe Gln Glu Glu His Arg Lys
```

```
           210                 215                 220
Ala Glu Glu Leu Leu Ala Ala Ala Gln Arg His Gln Gln Leu Gln
225                 230                 235                 240

Gln Lys Cys Gln Gln Gln Gln Lys Arg Gln Arg Leu Lys Glu Glu
                245                 250                 255

Leu Glu Lys His Gly Met Gln Val Pro Ala Gln Ala Gln Ser Thr Gln
                260                 265                 270

Glu Glu Glu Ala Gly Pro Gly Asp Val Ala Pro Arg Pro Gly Arg Pro
            275                 280                 285

Val Thr Trp Trp Ser
    290
```

<210> SEQ ID NO 24
<211> LENGTH: 51
<212> TYPE: PRT
<213> ORGANISM: Homo sapiens

<400> SEQUENCE: 24

```
Gln Asp Thr Ser Ser Gln Lys Ile Glu Asp Leu Met Glu Met Val Gln
1               5                   10                  15

Lys Leu Gln Lys Val Gly Ser Leu Glu Pro Arg Val Glu Val Leu Ile
            20                  25                  30

Asn Arg Ile Asn Glu Val Gln Gln Ala Lys Lys Ala Asn Lys Asp
        35                  40                  45

Leu Gly Glu
    50
```

<210> SEQ ID NO 25
<211> LENGTH: 29
<212> TYPE: PRT
<213> ORGANISM: Homo sapiens

<400> SEQUENCE: 25

```
Gln Asp Thr Ser Ser Gln Lys Ile Glu Asp Leu Met Glu Met Val Gln
1               5                   10                  15

Lys Leu Gln Lys Val Gly Ser Leu Glu Pro Arg Val Glu
            20                  25
```

<210> SEQ ID NO 26
<211> LENGTH: 45
<212> TYPE: PRT
<213> ORGANISM: Homo sapiens

<400> SEQUENCE: 26

```
Gln Gln Ala Lys Lys Ala Asn Lys Asp Leu Gly Glu Ala Arg Thr
1               5                   10                  15

Ile Cys Glu Ala Leu Gln Lys Glu Leu Asp Ser Leu His Gly Glu Lys
            20                  25                  30

Val His Leu Lys Glu Ile Leu Ser Lys Lys Gln Glu Thr
        35                  40                  45
```

<210> SEQ ID NO 27
<211> LENGTH: 39
<212> TYPE: PRT
<213> ORGANISM: Homo sapiens

<400> SEQUENCE: 27

```
Gln Glu Lys Glu Ser Glu Ala His Arg Lys His Thr Met Leu Gln Glu
1               5                   10                  15
```

```
Cys Lys Glu Arg Ile Ser Ala Leu Asn Leu Gln Ile Glu Glu Glu Lys
            20                  25                  30

Asn Lys Gln Arg Gln Leu Arg
        35

<210> SEQ ID NO 28
<211> LENGTH: 68
<212> TYPE: PRT
<213> ORGANISM: Homo sapiens

<400> SEQUENCE: 28

Glu Gln Leu Glu Asp Leu Met Gly Gln His Lys Asp Leu Trp Asp Phe
 1               5                  10                  15

His Met Pro Glu Arg Leu Ala Lys Glu Ile Cys Ala Leu Asp Ser Ser
            20                  25                  30

Lys Glu Gln Leu Leu Lys Glu Glu Lys Leu Val Lys Ala Thr Leu Glu
        35                  40                  45

Asp Val Lys His Gln Leu Cys Ser Leu Cys Gly Ala Glu Gly Pro Ser
    50                  55                  60

Thr Leu Asp Glu
65

<210> SEQ ID NO 29
<211> LENGTH: 53
<212> TYPE: PRT
<213> ORGANISM: Homo sapiens

<400> SEQUENCE: 29

Arg Ser Gln Glu Ala Ala Ala Thr Val Gln Leu Phe Gln Gly Glu His
 1               5                  10                  15

Arg Lys Ala Glu Glu Leu Leu Ala Ala Ala Ala Gln Arg His Gln Gln
            20                  25                  30

Leu Gln Gln Lys Cys Gln Gln Gln Gln Lys Arg Gln Arg Leu Lys
        35                  40                  45

Glu Glu Leu Glu Lys
    50

<210> SEQ ID NO 30
<211> LENGTH: 49
<212> TYPE: PRT
<213> ORGANISM: Homo sapiens

<400> SEQUENCE: 30

Gln Gln Lys Cys Gln Gln Gln Gln Lys Arg Gln Arg Leu Lys Glu
 1               5                  10                  15

Glu Leu Glu Lys His Gly Met Gln Val Pro Ala Gln Ala Gln Ser Thr
            20                  25                  30

Gln Glu Glu Glu Ala Gly Pro Gly Asp Val Ala Pro Arg Pro Gly Arg
        35                  40                  45

Pro

<210> SEQ ID NO 31
<211> LENGTH: 64
<212> TYPE: PRT
<213> ORGANISM: Homo sapiens

<400> SEQUENCE: 31

Asp Leu Gly Glu Ala Arg Thr Ile Cys Glu Ala Leu Gln Lys Glu Leu
 1               5                  10                  15
```

-continued

Asp Ser Leu His Gly Glu Lys Val His Leu Lys Glu Ile Leu Ser Lys
            20                  25                  30

Lys Gln Glu Thr Leu Arg Ile Leu Arg Leu His Cys Gln Glu Lys Glu
        35                  40                  45

Ser Glu Ala His Arg Lys His Thr Met Leu Gln Glu Cys Lys Glu Arg
    50                  55                  60

<210> SEQ ID NO 32
<211> LENGTH: 56
<212> TYPE: PRT
<213> ORGANISM: Homo sapiens

<400> SEQUENCE: 32

Glu Glu Glu Lys Asn Lys Gln Arg Gln Leu Arg Leu Ala Phe Glu Glu
1               5                   10                  15

Gln Leu Glu Asp Leu Met Gly Gln His Lys Asp Leu Trp Asp Phe His
            20                  25                  30

Met Pro Glu Arg Leu Ala Lys Glu Ile Cys Ala Leu Asp Ser Ser Lys
        35                  40                  45

Glu Gln Leu Leu Lys Glu Glu Lys
    50                  55

<210> SEQ ID NO 33
<211> LENGTH: 48
<212> TYPE: PRT
<213> ORGANISM: Homo sapiens

<400> SEQUENCE: 33

Thr Leu Glu Asp Val Lys His Gln Leu Cys Ser Leu Cys Gly Ala Glu
1               5                   10                  15

Gly Pro Ser Thr Leu Asp Glu Gly Leu Phe Leu Arg Ser Gln Glu Ala
            20                  25                  30

Ala Ala Thr Val Gln Leu Phe Gln Glu His Arg Lys Ala Glu Glu
        35                  40                  45

<210> SEQ ID NO 34
<211> LENGTH: 33
<212> TYPE: PRT
<213> ORGANISM: Homo sapiens

<400> SEQUENCE: 34

Glu Glu Leu Glu Lys His Gly Met Gln Val Pro Ala Gln Ala Gln Ser
1               5                   10                  15

Thr Gln Glu Glu Glu Ala Gly Pro Gly Asp Val Ala Pro Arg Pro Gly
            20                  25                  30

Arg

<210> SEQ ID NO 35
<211> LENGTH: 44
<212> TYPE: PRT
<213> ORGANISM: Homo sapiens

<400> SEQUENCE: 35

Glu Gly Pro Ser Thr Leu Asp Glu Gly Leu Phe Leu Arg Ser Gln Glu
1               5                   10                  15

Ala Ala Ala Thr Val Gln Leu Phe Gln Glu His Arg Lys Ala Glu
            20                  25                  30

Glu Leu Leu Ala Ala Ala Ala Gln Arg His Gln Gln
        35                  40

<210> SEQ ID NO 36
<211> LENGTH: 32
<212> TYPE: PRT
<213> ORGANISM: Homo sapiens

<400> SEQUENCE: 36

Lys Val Gly Ser Leu Glu Pro Arg Val Glu Val Leu Ile Asn Arg Ile
 1               5                  10                  15

Asn Glu Val Gln Gln Ala Lys Lys Ala Asn Lys Asp Leu Gly Glu
            20                  25                  30

<210> SEQ ID NO 37
<211> LENGTH: 40
<212> TYPE: PRT
<213> ORGANISM: Homo sapiens

<400> SEQUENCE: 37

Glu Cys Lys Glu Arg Ile Ser Ala Leu Asn Leu Gln Ile Glu Glu Glu
 1               5                  10                  15

Lys Asn Lys Gln Arg Gln Leu Arg Leu Ala Phe Glu Glu Gln Leu Glu
            20                  25                  30

Asp Leu Met Gly Gln His Lys Asp
            35                  40

<210> SEQ ID NO 38
<211> LENGTH: 65
<212> TYPE: PRT
<213> ORGANISM: Homo sapiens

<400> SEQUENCE: 38

Lys Lys Gln Glu Thr Leu Arg Ile Leu Arg Leu His Cys Gln Glu Lys
 1               5                  10                  15

Glu Ser Glu Ala His Arg Lys His Thr Met Leu Gln Glu Cys Lys Glu
            20                  25                  30

Arg Ile Ser Ala Leu Asn Leu Gln Ile Glu Glu Lys Asn Lys Gln
            35                  40                  45

Arg Gln Leu Arg Leu Ala Phe Glu Glu Gln Leu Glu Asp Leu Met Gly
    50                  55                  60

Gln
65

<210> SEQ ID NO 39
<211> LENGTH: 24
<212> TYPE: DNA
<213> ORGANISM: Homo sapiens

<400> SEQUENCE: 39
tgtgcctcac tttcctttc ctgg                                          24

<210> SEQ ID NO 40
<211> LENGTH: 23
<212> TYPE: DNA
<213> ORGANISM: Homo sapiens

<400> SEQUENCE: 40
taaagaccta ggagaggccc gga                                          23

<210> SEQ ID NO 41
<211> LENGTH: 293
<212> TYPE: DNA
<213> ORGANISM: Mus musculis -continued

```
<400> SEQUENCE: 41
agctgaggaa gtggagcagt atggccacca gaccgcagcc gttgggtatg gagcccgagg      60
gtcagcagac ctgctccacg ggcctgaggg ggccagaggg cagtatgggt ccacacagaa     120
aattgaagac ttaatggaca tggtgaaaaa gttgcagaaa gtgggaagcc tagagccccg     180
gattgaggtc ctgattaacc gtattaatga ggttcagcaa ggtaaagcag aaaagaaagc     240
cagtgaggag cttggagagg cccagactgt ctgggacaac ctgcagaagg gac            293
```

EDUCATIONAL KIT AND METHOD CONTAINING NOVEL ALPHA HELICAL PROTEIN-34

This claims the benefit under 35 U.S.C. §119 (e) of the filing date of U.S. Provisional Patent Application No. 60/162,623, filed Oct. 29, 1999.

BACKGROUND OF THE INVENTION

To teach basic molecular biology full-length cDNAs are need to be provided to the students in educational kits for use in laboratory practica. Students can then use these full-length cDNAs to learn and practice to make expression vector, learn to transfect the cells and produce full-length protein. The DNA that encodes the protein can also be used to teach Northern blot analysis to learn how to determine in which tissues the mRNA is produced. Having identified where the mRNA is expressed, the mRNA in the tissue can then be isolated and cDNA produced. The student can then learn how to make a cDNA library. The novel polynucleotide can then be used to teach at student how to probe a cDNA library to determine which clone or clones contain the newly discoverd polynucleotide. The novel polynucleotide can also be used to teach chromosome localization.

To teach protein chemistry, a novel full-length protein can be used so the student can have practical learning experiences in protein purification procedures, protein re-folding when the protein is produced in prokaryotic host cells, and how to make both monoclonal and polyclonal antibodies.

Antibodies that bind to mature protein can also be used to learn how to make affinity purification columns, to do enzyme-linked immunoabsorbent assay (ELISA).

Especially useful novel polynucleotides for educational lab kits are those that encode protein that are hormones or growth factors. Hormones and growth factors influence cellular metabolism by binding to proteins. Proteins may be integral membrane proteins that are linked to signaling pathways within the cell, such as second messenger systems. Other classes of proteins are soluble molecules, such as the transcription factors.

Of particular interest are cytokines, molecules that promote the proliferation, maintenance, survival or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils.

Even though many polynucleotide sequences that encode full-length, naturally occurring proteins are known, there is a need for the discovery of new full-length cDNAs or genomic DNA that encode for naturally-occurring proteins because each new sequence has unique features, such as unique enzyme-restriction sites, which are useful in increasing the analytical and technical skill of the student. There is also a need to discover new full-length and mature, naturally occurring polypeptides and proteins to teach protein chemistry and purification.

DESCRIPTION OF THE INVENTION

The present invention addresses this need by providing a novel education kit. The educational kit is comprised of one or more containers that contain at least one of the following, a polynucleotide that encodes a mature Zalpha34 polypeptide, full-length or mature Zalpha34 polypeptide, antibodies that specifically bind to a Zalpha34 polypeptide, a cloning or expression vector containing a polynucleotide that encodes a Zalpha34 polypeptide, or host cells, either prokaryotic or eukaryotic that have been transformed or transfected with an expression or cloning vector containing a polynucleotide that encodes a mature Zalpha34 polypeptide.

The present invention also fills this need by providing for the novel polypeptides, isolated polynucleotides that encode the polypeptides and related compositions and methods that can be used in educational kits. Within one aspect, the present invention provides an isolated polynucleotide encoding a mammalian alpha helical polypeptide termed 'Secreted alpha protein-34', hereinafter referred to as "Zalpha34". The mouse Zalpha34 polypeptide (SEQ ID NO: 2) is encoded by SEQ ID NO: 1. The molecular weight of SEQ ID NO: 2 is about 32,328 Daltons (D). The polypeptide of SEQ ID NO: 2 has a signal sequence extending from amino acid residue 1 to and including amino acid residue 27. Thus, the mature sequence extends from amino acid residue 28 to and including amino acid residue 331 of SEQ ID NO: 2. The mature sequence is also represented by SEQ ID NO: 3. The human Zalpha34 polypeptide (SEQ ID NO: 22) is encoded by the polynucleotide of SEQ ID NO: 21. The polypeptide of SEQ ID NO: 22 has a signal sequence extending from amino acid residue 1 to and including amino acid residue 25. Thus, the mature sequence extends from amino acid residue 26 to and including amino acid residue 331 and is also represented by SEQ ID NO:23.

Within another aspect of the invention there is provided an expression vector comprising (a) a transcription promoter; (b) a DNA segment encoding a Zalpha34 polypeptide, and (c) a transcription terminator, wherein the promoter, DNA segment, and terminator are operably linked. Within another aspect of the invention there is provided a cultured cell into which has been introduced an expression vector as disclosed above, wherein said cell expresses a protein polypeptide encoded by the DNA segment.

Within a further aspect of the invention there is provided a chimeric polypeptide consisting essentially of a first portion and a second portion joined by a peptide bond. The first portion of the chimeric polypeptide consists essentially of (a) a Zalpha34 polypeptide as shown in SEQ ID NO: 2 (b) allelic variants of SEQ ID NOs: 2, 3, 22 or 23; and (c) protein polypeptides that are at least 90% identical to (a) or (b). The second portion of the chimeric polypeptide consists essentially of another polypeptide such as an affinity tag. Within one embodiment the affinity tag is an immunoglobulin $F_c$ polypeptide. The invention also provides expression vectors encoding the chimeric polypeptides and host cells transfected to produce the chimeric polypeptides.

Within an additional aspect of the invention there is provided an antibody that specifically binds to a Zalpha34 polypeptide as disclosed above, and also an anti-idiotypic antibody that neutralizes the antibody to a Zalpha34 polypeptide.

An additional embodiment of the present invention relates to a peptide or polypeptide that has the amino acid sequence of an epitope-bearing portion of a Zalpha34 polypeptide having an amino acid sequence described above. Peptides or polypeptides having the amino acid sequence of an epitope-bearing portion of a Zalpha34 polypeptide of the present invention include portions of such polypeptides with at least nine, preferably at least 15 and more preferably at least 30 to 50 amino acids, although epitope-bearing polypeptides of any length up to and including the entire amino acid sequence of a polypeptide of the present invention described above are also included in the present invention. Examples of epitope-bearing polypeptides of the present invention are SEQ ID NOs: 4–20 for mouse Zalpha34 and SEQ ID NOs: 24–38 of human Zalpha34. Also claimed are any of these polypeptides that are fused to another polypeptide or carrier molecule.

The teachings of all the references cited herein are incorporated in their entirety herein by reference.

1. Overview

The present invention provides novel cytokine polypeptides/proteins. The novel cytokine, termed "alpha helical protein-34" hereinafter referred to as "Zalpha34" was discovered and identified to be a cytokine by the presence of polypeptide and polynucleotide features characteristic of four-helix-bundle cytokines (e.g., erythropoietin, thrombopoietin, G-CSF, IL-2, IL-4, leptin and growth hormone).

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally occurring nucleotides (such as DNA and RNA), or analogs of naturally occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. One can link nucleic acid monomers by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (ie., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cunmmings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent, if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. For example, the Zalpha34 regulatory element preferentially induces gene expression in placental, tracheal, and uterine tissues, as opposed to lung, brain, liver, kidney, spleen, thymus, prostate, testis, ovary, small intestine, and pancreas tissues.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (ie., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the,core promoter.

A "recombinant host" is a cell that contains a heterologous nucleic acid molecule, such as a cloning vector or expression vector. In the present context, an example of a recombinant host is a cell that produces Zalpha34 from an expression vector. In contrast, Zalpha34 can be produced by a cell that is a "natural source" of Zalpha34, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a Zalpha34 polypeptide fused with a polypeptide that binds an affinity matrix. Such a fusion protein provides a means to isolate large quantities of Zalpha34 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effect or domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal or N-terminal" and "carboxyl-terminal or C-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-Zalpha34 antibody, and thus, an anti-idiotype antibody mimics an epitope of Zalpha34.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-Zalpha34 monoclonal antibody fragment binds with an epitope of Zalpha34.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom that is conjugated to an antibody moiety to produce a conjugate that is useful for therapy. Examples of therapeutic agents include drugs, toxins, immunomodulators, chelators, boron compounds, photoactive agents or dyes, and radioisotopes.

A "detectable label" is a molecule or atom that can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A [Nilsson et al., *EMBO J.* 4:1075 (1985); Nilsson et al., *Methods Enzymol.* 198:3 (1991)], glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain.

See, in general, Ford et al., *Protein Expression and Purification* 2:95 (1991). DNAs encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a therapeutic agent. Examples of therapeutic agents suitable for such fusion proteins include immuno-modulators ("antibody-immunomodulator fusion protein") and toxins ("antibody-toxin fusion protein").

A "tumor associated antigen" is a protein normally not expressed, or expressed at lower levels, by a normal counterpart cell. Examples of tumor associated antigens include alpha-fetoprotein, carcinoembryonic antigen, and Her-2/neu. Many other illustrations of tumor-associated antigens are known. See, for example, Urban et al., *Ann. Rev. Immunol.* 10:617 (1992).

As used herein, an "infectious agent" denotes both microbes and parasites. A "microbe" includes viruses, bacteria, rickettsia, mycoplasma, protozoa, fungi and like microorganisms. A "parasite" denotes infectious, generally microscopic or very small multicellular invertebrates, or ova or juvenile forms thereof, which are susceptible to immune-mediated clearance or lytic or phagocytic destruction, such as malarial parasites, spirochetes, and the like.

An "infectious agent antigen" is an antigen associated with an infectious agent.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide that will bind a major histocompatibility complex molecule to form an MHC-peptide complex, which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell that binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for Zalpha34" or a "Zalpha34 anti-sense oligonucleotide" is an oligonucleotide having a sequence (a) capable of forming a stable triplex with a portion of the Zalpha34 gene, or (b) capable of forming a stable duplex with a portion of an mRNA transcript of the Zalpha34 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant human Zalpha34 gene" refers to nucleic acid molecules that encode a polypeptide having an amino acid sequence that is a modification of SEQ ID NO: 2. Such variants include naturally-occurring polymorphisms of Zalpha34 genes, as well as synthetic genes that contain conservative amino acid substitutions of the amino acid sequence of SEQ ID NOs: 2, 3, 22 or 23. Additional variant forms of Zalpha34 genes are nucleic acid molecules that contain insertions or deletions of the nucleotide sequences described herein. A variant Zalpha34 gene can be identified by determining whether the gene hybridizes with a nucleic acid molecule having the nucleotide sequence of SEQ ID NO: 1, or its complement, under stringent conditions.

Alternatively, variant Zalpha34 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASER-GENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123–151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant Zalpha34 gene or variant Zalpha34 polypeptide, a variant gene or polypeptide encoded by a variant gene is functionally characterized by either its anti-viral or anti-proliferative activities, or by the ability to bind specifically to an anti-Zalpha34 antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

Due to the imprecision of standard analytical methods, molecular weights and lengths of polymers are understood to be approximate values. When such a value is expressed as "about" X or "approximately" X, the stated value of X will be understood to be accurate to ±10%.

3. POLYNUCLEOTIDES:

The present invention also provides polynucleotide molecules including DNA and RNA molecules that encode the Zalpha34 polypeptides disclosed herein. Those skilled in the art will readily recognize that, in view of the degeneracy of the genetic code, considerable sequence variation is possible among these polynucleotide molecules.

Polynucleotides, generally a cDNA sequence, of the present invention encode the described polypeptides herein. A cDNA sequence that encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;

Cysteine (Cys) is encoded by TGC or TGT;

Aspartic acid (Asp) is encoded by GAC or GAT;

Glutamic acid (Glu) is encoded by GAA or GAG;

Phenylalanine (Phe) is encoded by TTC or TTT;

Glycine (Gly) is encoded by GGA, GGC, GGG or GGT;

Histidine (His) is encoded by CAC or CAT;

Isoleucine (Ile) is encoded by ATA, ATC or ATT;

Lysine (Lys) is encoded by AAA, or AAG;

Leucine (Leu) is encoded by TTA, TTG, CTA, CTC, CTG or CTT;

Methionine (Met) is encoded by ATG;

Asparagine (Asn) is encoded by AAC or AAT;

Proline (Pro) is encoded by CCA, CCC, CCG or CCT;

Glutarnine (Gln) is encoded by CAA or CAG;

Arginine (Arg) is encoded by AGA, AGG, CGA, CGC, CGG or CGT;

Serine (Ser) is encoded by AGC, AGT, TCA, TCC, TCG or TCT;

Threonine (Thr) is encoded by ACA, ACC, ACG or ACT;

Valine (Val) is encoded by GTA, GTC, GTG or GTT;

Tryptophan (Trp) is encoded by TGG; and

Tyrosine (Tyr) is encoded by TAC or TAT.

It is to be recognized that according to the present invention, when a polynucleotide is claimed as described herein, it is understood that what is claimed are both the sense strand, the anti-sense strand, and the DNA as double-stranded having both the sense and anti-sense strand annealed together by their respective hydrogen bonds. Also claimed is the messenger RNA (mRNA) that encodes the polypeptides of the president invention, and which mRNA is encoded by the cDNA described herein.

Messenger RNA (mRNA) will encode a polypeptide using the same codons as those defined herein, with the exception that each thymine nucleotide (T) is replaced by a uracil nucleotide (U).

One of ordinary skill in the art will also appreciate that different species can exhibit "preferential codon usage." In general, see, Grantham, et al., *Nuc. Acids Res.* 8:1893–1912 (1980); Haas, et al. *Curr. Biol.* 6:315–324 (1996); Wain-Hobson, et al., *Gene* 13:355–364 (1981); Grosjean and Fiers, *Gene* 18:199–209 (1982); Holm, *Nuc. Acids Res.* 14:3075–3087 (1986); Ikemura, *J. Mol. Biol.* 158:573–597 (1982). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Sequences containing preferential codons can be tested and optimized for expression in various species, and tested for functionality as disclosed herein.

Within preferred embodiments of the invention the isolated polynucleotides will hybridize to similar sized regions of SEQ ID NOs: 1 or 21, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted the isolated polynucleotides of the present invention include DNA and RNA. Methods for preparing DNA and RNA are well known in the art. In general, RNA is isolated from a tissue or cell that produces large amounts of Zalpha34 RNA such as a testis cDNA library. Such tissues and cells are identified by Northern blotting, Thomas, *Proc. Natl. Acad. Sci. USA* 77:5201 (1980) and are discussed below. Total RNA can be prepared using guanidine HCl extraction followed by isolation by centrifugation in a CsCl gradient, Chirgwin et al., *Biochemistry* 18:52–94 (1979). Poly (A)$^+$ RNA is prepared from total RNA using the method of Aviv and Leder, *Proc. Natl. Acad. Sci. USA* 69:1408–1412 (1972). Complementary DNA (cDNA) is prepared from poly(A)$^+$ RNA using known methods. In the alternative, genomic DNA can be isolated. Polynucleotides encoding Zalpha34 polypeptides are then identified and isolated by, for example, hybridization or PCR.

Nucleic acid molecules encoding a human Zalpha34 gene can be obtained by screening a human cDNA or genomic library using polynucleotide probes based upon SEQ ID NOs: 1 or 21. These techniques are standard and well established.

As an illustration, a nucleic acid molecule that encodes a human Zalpha34 gene can be isolated from a human cDNA library. In this case, the first step would be to prepare the cDNA library by isolating RNA from testis. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenoychloroform to remove proteins, and separating RNA from the remaining impurities by selective precipitation with lithium chloride [see, for example, Ausubel et al. (eds.), *Short Protocols in Molecular Biology*, 3$^{rd}$ Edition, pages 4-1 to 4-6 (John Wiley & Sons 1995)] ["Ausubel (1995)"]; Wu et al., *Methods in Gene Biotechnology*, pages 33–41 (CRC Press, Inc. 1997) "Wu (1997)".

Alternatively, total RNA can be isolated from mammary epithelial tissue by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4-1 to 4-6; Wu (1997) at pages 33–41).

In order to construct a cDNA library, poly(A)$^+$ RNA must be isolated from a total RNA preparation. Poly(A)$^+$ RNA can be isolated from total RNA using the standard technique of oligo(dT)-cellulose chromatography (see, for example, Aviv and Leder, *Proc. Nat'l Acad. Sci. USA* 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41–46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA blibrary. For example, a cDNA library can be prepared in a vector derived from bacteriophage, such as a λgt10 vector. See, for example, Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47–52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va).

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A human genomic library can be prepared by means well known in the art [see, for example, Ausubel (1995) at pages 5-1 to 5-6; Wu (1997) at pages 307–327]. Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well known in the art [see, for example, Ausubel (1995) at pages 5-1 to 5-6; Wu (1997) at pages 307–327].

Nucleic acid molecules that encode a human Zalpha34 gene can also be obtained using the polymerase chain reaction (PCR) with oligonucleotide primers having nucleotide sequences that are based upon the nucleotide sequences of the human Zalpha34 gene, as described herein. General methods for screening libraries with PCR are provided by, for example, Yu et al., "Use of the Polymerase Chain Reaction to Screen Phage Libraries," in *Methods in Molecular Biology, Vol.* 15: *PCR Protocols: Current Methods and Applications*, White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol.* 15: *PCR Protocols: Current Methods and Applications*, White (ed.), pages 317–337 (Humana Press, Inc. 1993).

Alternatively, human genomic libraries can be obtained from commercial sources such as Research Genetics (Huntsville, Ala.) and the American Type Culture Collection (Manassas, Va.).

A library containing cDNA or genomic clones can be screened with one or more polynucleotide probes based upon SEQ ID NO: 1, using standard methods [see, for example, Ausubel (1995) at pages 6-1 to 6-11].

Anti-Zalpha34 antibodies, produced as described below, can also be used to isolate DNA sequences that encode human Zalpha34 genes from cDNA libraries. For example, the antibodies can be used to screen λgtl 1 expression libraries, or the antibodies can be used for immunoscreening following hybrid selection and translation (see, for example, Ausubel (1995) at pages 6-12 to 6-16; Margolis. et al., "Screening λ expression libraries with antibody and protein probes," in *DNA Cloning* 2: *Expression Systems, 2nd Edition*, Glover et al. (eds.), pages 1–14 (Oxford University Press 1995)).

As an alternative, a Zalpha34 gene can be obtained by synthesizing nucleic acid molecules using mutually priming long oligonucleotides and the nucleotide sequences described herein [see, for example, Ausubel (1995) at pages 8-8 to 8-9]. Established techniques using the polymerase chain reaction provide the ability to synthesize DNA molecules at least two kilobases in length [Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol.* 15: *PCR Protocols: Current Methods and Applications*, White (ed.), pages 263–268, (Humana Press, Inc. 1993), and Holowachuk et al., *PCR Methods Appl.* 4:299 (1995)].

The polynucleotides of the present invention can also be synthesized with DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles & Applications of Recombinant DNA*, (ASM Press, Washington, D.C. 1994); Itakura et al., *Annu. Rev. Biochem.* 53: 323–356 (1984) and Climie et al., *Proc. Natl. Acad. Sci. USA* 87:633–637 (1990).

The present invention further provides counterpart polypeptides and polynucleotides from other species (orthologs). These species include, but are not limited to mammalian, avian, amphibian, reptile, fish, insect and other vertebrate and invertebrate species. Of particular interest are Zalpha34 polypeptides from other mammalian species, including murine, porcine, ovine, bovine, canine, feline, equine, and other primate polypeptides. Orthologs of human Zalpha34 can be cloned using information and compositions provided by the present invention in combination with conventional cloning techniques. For example, a cDNA can be cloned using mRNA obtained from a tissue or cell type that expresses Zalpha34 as disclosed herein. Suitable sources of mRNA can be identified by probing Northern blots with probes designed from the sequences disclosed herein. A library is then prepared from mRNA of a positive tissue or cell line. A Zalpha34-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human Zalpha34 sequence disclosed herein. Within an additional method, the cDNA library can be used to transform or transfect host cells, and expression of the cDNA of interest can be detected with an antibody to Zalpha34 polypeptide. Similar techniques can also be applied to the isolation of genomic clones.

Those skilled in the art will recognize that the sequences disclosed in SEQ ID NOs: 1 and 21 represents a single alleles of mouse and human Zalpha34 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO: 1 or SEQ ID NO:21, including those containing silent mutations and those in which mutations result in amino acid sequence changes, are within the scope of the present invention, as are proteins which are allelic variants of SEQ ID NO:2 or SEQ ID NO:22. cDNAs generated from alternatively spliced mRNAs, which retain the properties of the Zalpha34 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zalpha34 polypeptides from other mammalian species, including murine, porcine, ovine, bovine, canine, feline, equine, and other primate polypeptides. Orthologs of human Zalpha34 can be cloned using information and compositions provided by the present invention in combination with conventional cloning techniques. For example, a cDNA can be cloned using mRNA obtained from a tissue or cell type that expresses Zalpha34 as disclosed herein. Suitable sources of mRNA can be identified by probing northern blots with probes designed from the sequences disclosed herein. A library is then prepared from mRNA of a positive tissue or cell line.

A Zalpha34-encoding cDNA can then be isolated by a variety of methods, such as by probing with a complete or partial human cDNA or with one or more sets of degenerate probes based on the disclosed sequences. A cDNA can also be cloned using the polymerase chain reaction with primers designed from the representative human Zalpha34 sequences disclosed herein. Within an additional method, the cDNA library can be used to transform or transfect host cells, and expression of the cDNA of interest can be detected with an antibody to Zalpha34 polypeptide. Similar techniques can also be applied to the isolation of genomic clones.

Those skilled in the art will recognize that the sequence disclosed in SEQ ID NO: 1 and 21 represent a single alleles of mouse and human Zalpha34, and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO: 1, including those containing silent mutations and those in which mutations result in amino acid sequence changes, are within the scope of the present invention, as are proteins which are allelic variants of SEQ ID NOs: 2, 3, 22 and 23. cDNA molecules generated from alternatively spliced mRNAs, which retain the properties of the Zalpha34 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within preferred embodiments of the invention, isolated nucleic acid molecules that encode human Zalpha34 can hybridize to nucleic acid molecules having the nucleotide sequence of SEQ ID NOs: 1, 21 or a sequence complementary thereto, under "stringent conditions." In general, stringent conditions are selected to be about 5° C. lower than the thermal melting point ($T_m$) for the specific sequence at a defined ionic strength and pH. The $T_m$ is the temperature (under defmed ionic strength and pH) at which 50% of the target sequence hybridizes to a perfectly matched probe.

As an illustration, a nucleic acid molecule encoding a variant Zalpha34 polypeptide can be hybridized with a nucleic acid molecule having the nucleotide sequence of SEQ ID NOs: 1 or 21 (or their respective complements) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100×Denhardt's solution: 2% (w/v) Ficoll 400, 2% (w/v) polyvinylpyrrolidone, and 2% (w/v) bovine.serum albumin), 10% dextran sulfate, and 20 $\mu$g/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant Zalpha34 polypeptide hybridize with a nucleic acid molecule having the nucleotide sequence of SEQ ID NOs: 1 or 21 (or its complement) under stringent washing conditions, in which the wash stringency is equivalent to 0.5×–2×SSC with 0.1% SDS at 55–65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant Zalpha34 polypeptide hybridize with a nucleic acid molecule having the nucleotide sequence of SEQ ID NOs: 1 or 21 (or its complement) under highly stringent washing conditions, in which the wash stringency is equivalent to 0.1x–0.2xSSC with 0.1% SDS at 50–65° C., including 0.1x–SSC with 0.1% SDS at 50° C., or 0.2xSSC with 0.1% SDS at 65° C.

The present invention also provides isolated Zalpha34 polypeptides that have a substantially similar sequence identity to the polypeptides of SEQ ID NOs: 2, 3, 22, 23 or their orthologs. The term "substantially similar sequence identity" is used herein to denote polypeptides having at least at least 90%, at least 95% or greater sequence identity to the sequences shown in SEQ ID NOs: 2, 3, 22 or 23 or their orthologs.

The present invention also contemplates Zalpha34 variant nucleic acid molecules that can be identified using two criteria: a determination of the similarity between the encoded polypeptide with the amino acid sequences of SEQ ID NOs: 2, 3, 22 or 23, and a hybridization assay, as described above. Such Zalpha34 variants include nucleic acid molecules (1) that hybridize with a nucleic acid molecule having the nucleotide sequence of SEQ ID NO: 1 or 21 (or their complements) under stringent washing conditions, in which the wash stringency is equivalent to 0.5x–2xSSC with 0.1% SDS at 55–65° C., and (2) that encode a polypeptide having at least 70%, at least 80%, at least 90%, at least 95% or greater than 95% sequence identity to the amino acid sequence of SEQ ID NO: 2, 3, 22 or 23. Alternatively, Zalpha34 variants can be characterized as nucleic acid molecules (1) that hybridize with a nucleic acid molecule having the nucleotide sequence of SEQ ID NO: 1 or 21 (or their complements) under highly stringent washing conditions, in which the wash stringency is equivalent to 0.1x–0.2xSSC with 0.1% SDS at 50–65° C., and (2) that encode a polypeptide having at least 95% or greater than 95% sequence identity to the amino acid sequence of SEQ ID NO:2.

The present invention also contemplates human Zalpha34 variant nucleic acid molecules identified by at least one of hybridization analysis and sequence identity determination, with reference to SEQ ID NOs: 1, 2, 3, 21, 22 or 23.

The present invention also provides isolated Zalpha34 polypeptides that are substantially homologous to the polypeptides of SEQ ID NO:3 or SEQ ID NO:23 and their orthologs. The term "substantially homologous" is used herein to denote polypeptides having 50%, preferably 60%, more preferably at least 80%, sequence identity to the sequences shown in SEQ ID NO: 2 or 22 or their orthologs. Such polypeptides will more preferably be at least 90% identical, and even more preferably 95% or more identical to SEQ ID NOs: 2 or 22 or their orthologs.) Percent sequence identity is determined by conventional methods. See, for example, Altschul et al., *Bull. Math. Bio.* 48: 603–616 (1986) and Henikoff and Henikoff, *Proc. Natl. Acad. Sci. USA* 89:10915–10919 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| W | -3 | -3 | -4 | -4 | -2 | -2 | -3 | -2 | -2 | -3 | -2 | -3 | -1 | 1 | -4 | -3 | -2 | 11 | | |
| T | 0 | -1 | 0 | -1 | -1 | -1 | -1 | -2 | -2 | -1 | -1 | -1 | -1 | -2 | -1 | 1 | 5 | | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms to align two amino acid sequences. The "FASTA" similarity search algorithm of Pearson and Lipman is a suitable protein alignment method for examining the level of identity shared by an amino acid sequence and the amino acid sequence of a putative variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions or deletions. The ten regions with the highest density of identities are then re-scored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974), which allows for amino acid insertions and deletions. Illustiative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more conservative amino acid changes, compared with the amino acid sequence of SEQ ID NOs: 2, 3, 22 or 23. The BLOSUM62 table is an amino acid substitution matrix derived from about 2,000 local multiple alignments of protein sequence segments, representing highly conserved regions of more than 500 groups of related proteins [Henikoff and Henikoff, *Proc. Nat'l Acad. Sci. USA* 89:10915 (1992)]. Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0,1,2, or 3. Preferred conservative amino acid substitutions are characterized by a BLOSUM62 value of at least 1 (e.g., 1,2 or 3), while more preferred conservative substitutions are characterized by a BLOSUM62 value of at least 2 (e.g., 2 or 3). Accordingly the present invention claims those polypeptides which are at least 90%, preferably 95% and most preferably 99% identical to SEQ ID NOs: 2, 3, 22 or 23 and which are able to stimulate antibody production in a mammal, and said antibodies are able to bind the native sequence of SEQ ID NOs: 2, 3, 22 or 23.

4. Polypeptides

Variant Zalpha34 polypeptides or substantially homologous Zalpha34 polypeptides are characterized as having one or more amino acid substitutions, deletions or additions. These changes are preferably of a minor nature, that is conservative amino acid substitutions (see Table 2) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag. The present invention thus includes polypeptides of from 20 to 30 amino acid residues that comprise a sequence that is at least 90%, preferably at least 95%, and more preferably 99% or more identical to the corresponding region of SEQ ID NO:4 or SEQ ID NO:23. Polypeptides comprising affinity tags can further comprise a proteolytic cleavage site between the Zalpha34 polypeptide and the affity tag. Preferred such sites include thrombin cleavage sites and factor Xa cleavage sites.

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention also provides polypeptide fragments or peptides comprising ah epitope-bearing portion of a Zalpha34 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about amino acids of SEQ ID NOs: 2, 3, 22 or 23. Such epitope-bearing peptides and polypeptides can be produced by fragmenting a Zalpha34 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997). Examples of such epitope-bearing polypeptides are polypeptides comprised of SEQ ID NOs: 4–20.

For any Zalpha34 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Zalpha34 variants based upon the nucleotide and amino acid sequences described herein. Accordingly, the present invention includes a computer-readable.medium encoded with a data structure that provides at least one of the following sequences: SEQ ID NOs: 1–38. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

5. Production of Zalpha34 Fusion Proteins and Conjugates

Fusion proteins of Zalpha34 can be used to express Zalpha34 in a recombinant host, and to isolate expressed Zalpha34. As described below, particular Zalpha34 fusion proteins also have uses in diagnosis and therapy.

One type of fusion protein comprises a peptide that guides a Zalpha34 polypeptide from a recombinant host cell. To direct a Zalpha34 polypeptide into the secretory pathway of a eukaryotic host cell, a secretory signal sequence (also known as a signal peptide, a leader sequence, prepro sequence or pre sequence) is provided in the Zalpha34 expression vector. While the secretory signal sequence may be derived from Zalpha34, a suitable signal sequence may also be derived from another secreted protein or synthesized de novo. The secretory signal sequence is operably linked to a Zalpha34-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of Zalpha34 or another protein produced by mammalian cells (e.g., tissue-type plasminogen activator signal sequence, as described, for example, in U.S. Pat. No. 5,641,655) is useful for expression of Zalpha34 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, 2$^{nd}$ Edition, Glover and Hames (eds.), pages 123–167 (Oxford University Press 1995).

In bacterial cells, it is often desirable to express a heterologous protein as a fusion protein to decrease toxicity, increase stability, and to enhance recovery of the expressed protein. For example, Zalpha34 can be expressed as a fusion protein comprising a glutathione S-transferase polypeptide. Glutathione S-transferase fusion proteins are typically soluble, and easily purifiable from *E. coli* lysates on immobilized glutathione columns. In similar approaches, a Zalpha34 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, 2$^{nd}$ Edition, Glover and Hames (Eds.), pages 15–58 (Oxford University Press 1995). In addition, commercially available expression systems are available. For example, the PINPOINT Xa protein purification system (Promega Corporation;

Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

The present invention also contemplates that the use of the secretory signal sequence contained in the Zalpha34 polypeptides of the present invention to direct other polypeptides into the secretory pathway. A signal fusion polypeptide can be made wherein a secretory signal sequence derived from amino acid residues 1 to 27 of SEQ ID NO:2 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in a transgenic animal or in a cultured recombinant host to direct peptides through the secretory pathway. With regard to the latter, exemplary polypeptides include pharmaceutically active molecules such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, and IL-15), colony stimulating factors (e.g., granulocyte-colony stimulating factor (G-CSF) and granulocyte macrophage-colony stimulating factor (GM-CSF)), interferons (e.g., interferons-α, -β, -γ, -ω, -δ, and -τ), the stem cell growth factor designated "S1 factor," erythropoietin, and thrombopoietin. The Zalpha34 secretory signal sequence contained in the fusion polypeptides of the present invention is preferably fused amino-terminally to an additional peptide to direct the additional peptide into the secretory pathway. Fusion proteins comprising a Zalpha34 secretory signal sequence can be constructed using standard techniques.

Another form of fusion protein comprises a Zalpha34 polypeptide and an immunoglobulin heavy chain constant region, typically an $F_c$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:21). In this fusion protein, a preferred Fc moiety is a human γ4 chain, which is stable in solution and has little or no complement activating activity. Accordingly, the present invention contemplates an Zalpha34 fusion protein that comprises an Zalpha34 moiety and a human Fc fragment, wherein the C-terminus of the Zalpha34ε moiety is attached to the N-terminus of the Fc fragment via a peptide linker, such as a peptide consisting of the amino acid sequence of SEQ ID NO: 21. The Zalpha34 moiety can be a Zalpha34 molecule or a fragment thereof.

In another variation, an Zalpha34 fusion protein comprises an IgG sequence, an Zalpha34 moiety covalently joined to the aminoterminal end of the IgG sequence, and a signal peptide that is covalently joined to the aminoterminal of the Zalpha34 moiety, wherein the IgG sequence consists of the following elements in the following order: a hinge region, a $CH_2$ domain, and a $CH_3$ domain. Accordingly, the IgG sequence lacks a $CH_1$ domain. This general approach to producing fusion proteins that comprise both antibody and nonantibody portions has been described by LaRochelle et al., EP 742830 (WO 95/21258).

Fusion proteins comprising a Zalpha34 moiety and an Fc moiety can be used, for example, as an in vitro assay tool. For example, the presence of a Zalpha34 receptor in a biological sample can be detected using a Zalpha34-immunoglobulin fusion protein, in which the Zalpha34 moiety is used to target the cognate receptor, and a macromolecule, such as Protein A or anti-Fc antibody, is used to detect the bound fusion protein-receptor complex. Moreover, such fusion proteins can be used to identify agonists and antagonists that interfere with the binding of Zalpha34 to its receptor.

In addition, antibody-Zalpha34 fusion proteins, comprising antibody variable domains, are useful as therapeutic proteins, in which the antibody moiety binds with a target antigen, such as a tumor associated antigen. Methods of making antibody-cytokine fusion proteins are known to those of skill in the art. For example, antibody fusion proteins comprising an interleukin-2 moiety are described by Boleti et al., *Ann. Oncol.* 6:945 (1995), Nicolet et al., *Cancer Gene Ther.* 2:161 (1995), Becker et al., *Proc. Nat'l Acad. Sci. USA* 93:7826 (1996), Hank et al., *Clin. Cancer Res.* 2:1951 (1996), and Hu et al., *Cancer Res.* 56:4998 (1996). Moreover, Yang et al., *Hum. Antibodies Hybridomas* 6:129 (1995), and Xiang et al., *J. Biotechnol.* 53:3 (1997), describe fusion proteins that include an $F(ab')_2$ fragment and a tumor necrosis factor alpha moiety. Additional cytokine-antibody fusion proteins include IL-8, IL-12, or Zalpha34as the cytokine moiety (Holzer et al., *Cytokine* 8:214 (1996); Gillies et al., *J. Immunol.* 160:6195 (1998); Xiang et al., *Hum. Antibodies Hybridomas* 7:2 (1996)). Also see, Gillies, U.S. Pat. No. 5,650,150.

Moreover, using methods described in the art, hybrid Zalpha34 proteins can be constructed using regions or domains of the inventive (see, for example, Picard, *Cur. Opin. Biology* 5:511 (1994)). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure. Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. Moreover, such fusion proteins may exhibit other properties as disclosed herein. General methods for enzymatic and chemical cleavage of fusion proteins are described, for example, by Ausubel (1995) at pages 16–19 to 16–25.

The present invention also contemplates chemically modified Zalpha34 compositions, in which a Zalpha34 polypeptide is linked with a polymer. Typically, the polymer is water-soluble so that the Zalpha34 conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1–C10)alkoxy, or aryloxy derivatives thereof (see, for example, Harris, et al., U.S. Pat. No. 5,252,714). The polymer maybe branched or unbranched. Moreover, a mixture of polymers can be used to produce Zalpha34 conjugates.

Zalpha34 conjugates used for therapy should preferably comprise pharmaceutically acceptable water-soluble polymer moieties. Conjugation of interferons with water-soluble polymers has been shown to enhance the circulating half-life of the interferon, and to reduce the immunogenicity of the polypeptide [see, for example, Nieforth et al., *Clin. Pharmacol. Ther.* 59:636 (1996), and Monkarsh et al., *Anal. Biochem.* 247:434 (1997)].

Suitable water-soluble polymers include polyethylene glycol (PEG), monomethoxy-PEG, mono-(C1–C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A Zalpha34 conjugate can also comprise a mixture of such water-soluble polymers.

One example of a Zalpha34 conjugate comprises a Zalpha34 moiety and a polyalkyl oxide moiety attached to the N-terminus of the Zalpha34 moiety. PEG is one suitable polyalkyl oxide. As an illustration, Zalpha34 can be modified with PEG, a process known as "PEGylation." PEGylation of Zalpha34 can be carried out by any of the PEGylation reactions known in the art [see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)]. For example, PEGylation can be performed by an acylation reaction or by an alkylation reaction with a reactive polyethylene glycol molecule. In an alternative approach, Zalpha34 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a Zalpha34 polypeptide. An example of an activated PEG ester is PEG esterified to N-hydroxysuccinimide. As used herein, the term "acylation" includes the following types of linkages between Zalpha34 and a water-soluble polymer: amide, carbamate, urethane, and the like. Methods for preparing PEGylated Zalpha34 by acylation will typically comprise the steps of (a) reacting an Zalpha34 polypeptide with PEG (such as a reactive ester of an aldehyde derivative of PEG) under conditions whereby one or more PEG groups attach to Zalpha34, and (b) obtaining the reaction product(s). Generally, the optimal reaction conditions for acylation reactions will be determined based upon known parameters and desired results. For example, the larger the ratio of PEG: Zalpha34, the greater the percentage of polyPEGylated Zalpha34 product.

The product of PEGylation by acylation is typically a polyPEGylated Zalpha34 product, wherein the lysine ε-amino groups are PEGylated via an acyl linking group. An example of a connecting linkage is an amide. Typically, the resulting Zalpha34 will be at least 95% mono-, di-, or tri-pegylated, although some species with higher degrees of PEGylation may be formed depending upon the reaction conditions. PEGylated species can be separated from unconjugated Zalpha34 polypeptides using standard purification methods, such as dialysis, ultrafiltration, ion exchange chromatography, affinity chromatography, and the like.

PEGylation by alkylation generally involves reacting a terminal aldehyde derivative of PEG with Zalpha34 in the presence of a reducing agent. PEG groups are preferably attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of Zalpha34 monopolymer conjugates.

Reductive alkylation to produce a substantially homogenous population of monopolymer Zalpha34 conjugate molecule can comprise the steps of: (a) reacting an Zalpha34 polypeptide with a reactive PEG under reductive alkylation conditions at a pH suitable to permit selective. modification of the α-amino group at the amino terminus of the Zalpha34, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer Zalpha34 conjugates, the reductive alkylation reaction conditions are those which permit the selective attachment of the water soluble polymer moiety to the N-terminus of Zalpha34. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:Zalpha34 need not be as large because more reactive groups are available. Typically, the pH will fall within the range of 3-9, or 3-6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to Zalpha34 will generally be in the range of 1:1 to 100:1. Typically, the molar ratio of water-soluble polymer to Zalpha34 will be 1:1 to 20:1 for polyPEGylation, and 1:1 to 5:1 for monoPEGylation.

Using the methods discussed herein, one of ordinary skill in the art can identify and/or prepare a variety of polypeptide fragments or variants of SEQ ID NO:3 or SEQ ID NO:23 or that retain the properties of the wild-type Zalpha34 protein. For any Zalpha34 polypeptide, including variants and fusion proteins, one of ordinary skill in the art can readily generate a fully degenerate polynucleotide sequence encoding that variant using the information set forth in Tables 1 and 2 above.

6. Production of Zalpha34 Polypeptides in Cultured Cells

The polypeptides of the present invention, including full-length polypeptides, functional fragments, and fusion proteins, can be produced in recombinant host cells following conventional techniques. To express a Zalpha34 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a Zalpha34 expression vector may comprise a Zalpha34 gene and a secretory sequence derived from a Zalpha34 gene or another secreted gene.

Zalpha34 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., *Som. Cell. Molec. Genet.* 12:555 (1986)]], rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as *actin, collagen, myosin*, and *metallothionein* genes.

Transcriptional regulatory sequences include a promoter region sufficient to direct the initiation of RNA synthesis. Suitable eukaryotic promoters include the promoter of the mouse *metallothionein* I gene [Hamer et al., *J. Molec. Appl. Genet.* 1:273 (1982)], the TK promoter of Herpes virus [McKnight, *Cell* 31:355 (1982)], the SV40 early promoter [Benoist et al., *Nature* 290:304 (1981)], the Rous sarcoma virus promoter (Gorman et al., *Proc. Nat'l Acad. Sci. USA* 79:6777 (1982)), the cytomegalovirus promoter [Foecking et al., *Gene* 45:101 (1980)], and the mouse mammary tumor virus promoter [see, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996)].

Alternatively, a prokaryotic promoter, such as the bacteriophage T3 RNA polymerase promoter, can be used to control Zalpha34 gene expression in mammalian cells if the prokaryotic promoter is regulated by a eukaryotic promoter [Zhou et al., Mol. Cell. Biol. 10:4529 (1990), and Kaufman et al., Nucl. Acids Res. 19:4485 (1991)].

An expression vector can be introduced into host cells using a variety of standard techniques including calcium phosphate transfection, liposome-mediated transfection, rnicroprojectile-mediated delivery, electroporation, and the like. Preferably, the transfected cells are selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multidrug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Zalpha34 polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid [for a review, see Becker et al., *Meth. Cell Biol.* 43:161 (1994), and Douglas and Curiel, *Science & Medicine* 4:44 (1997)]. Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein [see Garnier et al., *Cytotechnol.* 15:145 (1994)].

Zalpha34 genes may also be expressed in other higher eukaryotic cells, such as avian, fungal, insect, yeast, or plant cells. The baculovirus system provides an efficient means to introduce cloned Zalpha34 genes into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Zalpha34ϵ polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed Zalpha34 polypeptide, for example, a Glu-Glu epitope tag (Grussenmeyer et al., *Proc. Nat'l Acad. Sci.* 82:7952 (1985)). Using a technique known in the art, a transfer vector containing a Zalpha34 gene is transformed into *E. coli*, and screened for bacmids that contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed that replace the native Zalpha34 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67

(PharMingen: San Diego, Calif.) can be used in constructs to replace the native Zalpha34 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147–168 (The Humana Press, Inc. 1991), by Patel et al., "The baculovirus expression system," in *DNA Cloning 2: Expression Systems, 2nd Edition*, Glover et al. (eds.), pages 205–244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc 1996).

Fungal cells, including yeast cells, can also be used to express the genes described herein. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast-cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67–88 (CRC Press, 1993).

Alternatively, Zalpha34 genes can be expressed in prokaryotic host cells. Suitable promoters that can be used to express Zalpha34 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of Bacillus, Streptomyces promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Preferred prokaryotic hosts include *E. coli* and *Bacillus subtilus*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing a Zalpha34 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasniic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications, page* 137 (Wiley-Liss, Inc. 1995), and Georgiou, "Expression of Proteins in Bacteria," in *Protein Engineering: Principles and Practice*, Cleland et al. (eds.), page 101 [John Wiley & Sons, Inc. 1996)].

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in DNA *Cloning* 2: Expression Systems, *2nd Edition*, Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc. 1995).

7. Epitope-bearing Polypeptides

Another embodiment of the present invention provides for a peptide or polypeptide comprising an epitope-bearing portion of a Zalpha34 polypeptide of the invention. The epitope of the polypeptide portion is an immunogenic or antigenic epitope of a polypeptide of the invention. A region of a protein to which an antibody can bind is defined as an "antigenic epitope". See for instance, Geysen, H. M. et al., *Proc. Natl. Acad Sci. USA* 81:3998–4002 (1984). As to the selection of peptides or polypeptides bearing an antigenic epitope (i.e., that contain a region of a protein molecule to which an antibody can bind), it is well known in the art that relatively short synthetic peptides that mimic part of a protein sequence are routinely capable of eliciting an antiserum that reacts with the partially mimicked protein. See Sutcliffe, J. G. et al. *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer soluble peptides, especially those containing proline residues, usually are effective Examples of epitope-bearing polypeptides of the present invention are the polypeptides of comprised of the sequences of SEQ ID NOs: 4–20 for mouse Zalpha34 and the sequences of SEQ ID NOs: 24–38 for human Zalpha34.

Antigenic epitope-bearing peptides and polypeptides of the invention are therefore useful to raise polyclonal or monoclonal antibodies that bind specifically to a polypeptide of the invention. Antigenic epitope-bearing peptides and polypeptides of the present invention contain a sequence of at least nine, preferably between 15 to about 30 amino acids contained within the amino acid sequence of a polypeptide of the invention. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that react with the protein. Preferably, the amino acid sequence of the epitope-bearing peptide is selected to provide substantial solubility in aqueous solvents (i.e., the sequence includes relatively hydrophilic residues and hydrophobic residues are preferably avoided); and sequences, containing proline residues are particularly preferred. All of the polypeptides shown in the sequence listing contain antigenic epitopes to be used according to the present invention, however, specifically designed antigenic epitopes include the peptides defined by SEQ ID NOs:2–20 and 22–38. The present invention also provides polypeptide fragments or peptides comprising an epitope-bearing portion of a Zalpha1 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods [see, for example, Geysen et al., supra. See also U.S. Pat. No. 4,708,781 (1987) further describes how to identify a peptide bearing an immunogenic epitope of a desired protein.

8. Protein Isolation

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant Zalpha34 polypeptides (or chimeric Zalpha34 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods* (Pharmacia LKB Biotechnology, Uppsala, Sweden, 1988).

The polypeptides of the present invention can be isolated by exploitation of their properties. For example, immobilized metal ion adsorption (IMAC) chromatography can be used to purify histidine-rich proteins, including those comprising polyhistidine tags. Briefly, a gel is first charged with divalent metal ions to form a chelate, Sulkowski, *Trends in Biochem.* 3:1 (1985). Histidine-rich proteins will be adsorbed to this matrix with differing affities, depending upon the metal ion used, and will be eluted by competitive elution, lowering the pH, or use of strong chelating agents. Other methods of purification include purification of glycosylated proteins by lectin affinity chromatography and ion exchange chromatography. *Methods in Enzymol.*, Vol. 182, "Guide to Protein Purification", M. Deutscher, (ed.), page 529–539 (Acad. Press, San Diego, 1990). Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid Zalpha34 proteins, are constructed using regions or domains of the inventive Zalpha34, Sambrook et al., ibid., Altschul et al., ibid., Picard, *Cur. Opin. Biology*, 5:511 (1994). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between Zalpha34 of the present invention with the functionally equivalent domain(s) from another family member. Such domains include, but are not limited to, the secretory signal sequence, conserved, and significant domains or regions in this family. Such fusion proteins would be expected to have a biological functional profile that is the same or similar to polypeptides of the present invention or other known family proteins, depending on the fusion constructed. Moreover, such fusion proteins may exhibit other properties as disclosed herein.

9. Antagonists

Antagonists are useful as research reagents for characterizing sites of ligand-receptor interaction. Inhibitors of Zalpha34 activity (Zalpha34 antagonists) include anti-Zalpha34 antibodies and soluble Zalpha34 receptors, as well as other peptidic and non-peptidic agents (including ribozymes).

Zalpha34 can also be used to identify inhibitors (antagonists) of its activity. Test compounds are added to the assays disclosed herein to identify compounds that inhibit the activity of Zalpha34. In addition to those assays disclosed herein, samples can be tested for inhibition of Zalpha34 activity within a variety of assays designed to measure receptor binding or the stimulation/inhibition of Zalpha34-dependent cellular responses. For example, Zalpha34-responsive cell lines can be transfected with a reporter gene construct that is responsive to a Zalpha34-stimulated cellular pathway. Reporter gene constructs of this type are known in the art, and will generally comprise a Zalpha34-DNA response element operably linked to a gene encoding a protein that can be assayed, such as luciferase. DNA response elements can include, but are not limited to, cyclic AMP response elements (CRE), hormone response elements (HRE) insulin response element (IRE), Nasrin et al., *Proc. Natl. Acad. Sci. USA* 87:5273 (1990) and serum response elements (SRE) (Shaw et al. *Cell* 56: 563 (1989). Cyclic AMP response elements are reviewed in Roestler et al., *J. Biol. Chem.* 263 (19):9063 (1988) and Habener, *Molec. Endocrinol.* 4 (8):1087 (1990). Hormone response elements are reviewed in Beato, *Cell* 56:335 (1989). Candidate compounds, solutions, mixtures or extracts are tested for the ability to inhibit the activity of Zalpha34 on the target cells as evidenced by a decrease in Zalpha34 stimulation of reporter gene expression. Assays of this type will detect compounds that directly block Zalpha34 binding to cell-surface receptors, as well as compounds that block processes in the cellular pathway subsequent to receptor-ligand binding. In the alternative, compounds or other samples can be tested for direct blocking of Zalpha34 binding to receptor using Zalpha34 tagged with a detectable label (e.g., $^{125}$I, biotin, horseradish peroxidase, FITC, and the like). Within assays of this type, the ability of a test sample to inhibit the binding of labeled Zalpha34 to the receptor is indicative of inhibitory activity, which can be confirmed through secondary assays Receptors used within binding assays may be cellular receptors or isolated, immobilized receptors.

A Zalpha34 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify the ligand. For use in assays, the chimeras are bound to a support via the $F_c$ region and used in an ELISA format.

A Zalpha34 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229 (1991) and Cunningham and Wells, *J. Mol. Biol.* 234:554 (1993). A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity, Scatchard, *Ann. NY Acad. Sci.* 51: 660 (1949) and calorimetric assays, Cunningham et al., *Science* 253:545 (1991); Cunningham et al., *Science* 245:821 (1991).

10. Antibodies

Zalpha34 polypeptides can also be used to prepare antibodies that specifically bind to Zalpha34 epitopes, peptides or polypeptides. The Zalpha34 polypeptide or a fragment thereof serves as an antigen (immunogen) to inoculate an animal and elicit an immune response. Suitable antigens would be the Zalpha34 polypeptides of SEQ ID NOs: 2–20 and 22–38. Antibodies generated from this immune response can be isolated and purified as described herein. Methods for preparing and isolating polyclonal and monoclonal antibodies are well known in the art.

See, for example, Current Protocols in Immunology, Cooligan, et al. (eds.), National Institutes of Health, (John Wiley and Sons, Inc., 1995); Sambrook et al., *Molecular Cloning: A Laboratory Manual, Second Edition* (Cold Spring Harbor, N.Y., 1989); and Hurrell, J. G. R., Ed., *Monoclonal Hybridoma Antibodies: Techniques and Applications* (CRC Press, Inc., Boca Raton, Fla., 1982).

As would be evident to one of ordinary skill in the art, polyclonal antibodies can be generated from inoculating a variety of warm-blooded animals such as horses, cows, goats, sheep, dogs, chickens, rabbits, mice, and rats with a Zalpha34 polypeptide or a fragment thereof. The immunogenicity of a Zalpha34 polypeptide may be increased through the use of an adjuvant, such as alum (aluminum hydroxide) or Freund's complete or incomplete adjuvant. Polypeptides useful for immunization also include fusion polypeptides, such as fusions of Zalpha34 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to Zalpha34 protein or peptide, and selection of antibody display libraries in phage or similar vectors (for instance, through use of immobilized or labeled Zalpha34 protein or peptide). Genes encoding polypeptides having potential Zalpha34 polypeptide-binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides that interact with a known target, which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharnacia LKB Biotechnology Inc. (Piscataway, N.J.). Random peptide display libraries can be screened using the Zalpha34 sequences disclosed herein to identify proteins that bind to Zalpha34. These "binding proteins" which interact with Zalpha34 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as Zalpha34 "antagonists" to block Zalpha34 binding and signal transduction in vitro and in vivo.

Antibodies are determined to be specifically binding if: 1) they exhibit a threshold level of binding activity, and 2) they do not significantly cross-react with related polypeptide molecules of the prior art. First, antibodies herein specifically bind if they bind to a Zalpha34 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis.

Second, antibodies are determined to specifically bind if they do not significantly cross-react with related polypeptides. Antibodies do not significantly cross-react with related polypeptide molecules, for example, if they detect Zalpha34 but not known related polypeptides using a standard Western blot analysis-(Ausubel et al., ibid.). Examples of known related polypeptides are orthologs, proteins from the same species that are members of a protein family (e.g. IL-16), Zalpha34 polypeptides, and non-human Zalpha34. Moreover, antibodies may be "screened against" known related polypeptides to isolate a population that specifically binds to the inventive polypeptides. For example, antibodies raised to Zalpha34 are adsorbed to related polypeptides adhered to insoluble matrix; antibodies specific to Zalpha34 will flow through the matrix under the proper buffer conditions. Such screening allows isolation of polyclonal and monoclonal antibodies non-crossreactive to closely related polypeptides, *Antibodies: A Laboratory Manual*, Harlow and Lane (eds.) (Cold Spring Harbor Laboratory Press, 1988); *Current Protocols in Immunology*, Cooligan, et al. (eds.), National Institutes of Health (John Wiley and Sons, Inc., 1995). Screening and isolation of specific antibodies is well known in the art. See, *Fundamental Immunology*, Paul (eds.) (Raven Press, 1993); Getzoff et al., *Adv. in Immunol.* 43: 1–98 (1988); *Monoclonal Antibodies: Principles and Practice*, Goding, J. W. (eds.), (Academic Press Ltd., 1996); Benjamin et al., *Ann. Rev. Immunol.* 2: 67–101 (1984).

A variety of assays known to those skilled in the art can be utilized to detect antibodies which specifically bind to Zalpha34 proteins or peptides. Exemplary assays are described in detail in *Antibodies: A Laboratory Manual*, Harlow and Lane (Eds.) (Cold Spring Harbor Laboratory Press, 1988). Representative examples of such assays include: concurrent immunoelectrophoresis, radioimmunoassay, radioimmuno-precipitation, enzyme-linked inmmunosorbent assay (ELISA), dot blot or Western blot assay, inhibition or competition assay, and sandwich assay. In addition, antibodies can be screened for binding to wild-type versus mutant Zalpha34 protein or polypeptide.

Antibodies to Zalpha34 may be used for tagging cells that express Zalpha34 and for isolating Zalpha34 by affinity purification.

11. EDUCATIONAL KIT UTILITY OF ZALPHA34 POLYPEPTIDES, POLYNUCLEOTIDES AND ANTIBODIES.

Polynucleotides and polypeptides of the present invention will additionally find use as educational tools as a laboratory practicum kits for courses related to genetics and molecular biology, protein chemistry and antibody production and analysis. Due to its unique polynucleotide and polypeptide sequence molecules of Zalpha34 can be used as standards or as "unknowns" for testing purposes. For example, Zalpha34 polynucleotides can be used as an aid, such as, for example, to teach a student how to prepare expression constructs for bacterial, viral, and/or mammalian expression, including fusion constructs, wherein Zalpha34 is the gene to be expressed; for determining the restriction endonuclease cleavage sites of the polynucleotides; determining mRNA and DNA localization of Zalpha34 polynucleotides in tissues (i.e., by Northern and Southern blotting as well as polymerase chain reaction); and for identifying related polynucleotides and polypeptides by nucleic acid hybridization.

Zalpha34 polypeptides can be used educationally as an aid to teach preparation of antibodies; identifying proteins by Western blotting; protein purification; determining the weight of expressed Zalpha34 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., receptor binding, signal transduction, proliferation, and differentiation) in vitro and in vivo. Zalpha34 polypeptides can also be used to teach analytical skills such as mass spectrometry, circular dichroism to determine conformation, especially of the four alpha helices, x-ray crystallography to determine the three-dimensional structure in atomic detail, nuclear magnetic resonance spectroscopy to reveal the structure of proteins in solution. For example, a kit containing the Zalpha34 can be given to the student to analyze. Since the amino acid sequence would be known by the professor, the protein can be given to the student as a test to determine the skills or develop the skills of the student, the teacher would then know whether or not the student has correctly analyzed the polypeptide. Since every polypeptide is unique, the educational utility of Zalpha34 would be unique unto itself.

The antibodies that bind specifically to Zalpha34 can be used as a teaching aid to instruct students how to prepare affinity chromatography columns to purify Zalpha34, cloning and sequencing the polynucleotide that encodes an antibody and thus as a practicum for teaching a student how to design humanized antibodies. The Zalpha34 gene, polypeptide or antibody would then be packaged by reagent companies and sold to universities so that the students gain skill in art of molecular biology. Because each gene and protein is unique, each gene and protein creates unique challenges and learning experiences for students in a lab practicum. Such educational kits, containing the Zalpha34 gene, polypeptide or antibody, are considered within the scope of the present invention.

Chromosome Localization

A polynucleotide that encodes human Zalpha34 has been mapped to chromosome 10q26. The polynucleotide that encodes mouse Zalpha34 has been mapped to chromosome 7, linked to D&Mit46 at 69 cM.

Use of Zalpha34

Zalpha34 can be used administered to a male to promote spermatogenesis.

The invention is further illustrated by the following non-limiting examples.

EXAMPLE 1

Cloning of Mouse Zalpha34

In searching for polynucleotides that may have an alpha helical structure the Expressed Sequence Tag (EST) SEQ ID NO: 41 (Clone Id:IMAGE:515836, IMAGE CONSORTIUM was discovered in a testis cDNA library. The clone was ordered from Genome Systems of ST. Louis, Mo. and sequenced resulting in the sequences of SEQ ID NOs: 1 and 2.

EXAMPLE 2

The Cloning of Human Zalpha34

Full-length sequence was obtained from a clone isolated from an arrayed human testis cDNA/plasmid library. The library was screened by PCR using oligonucleotides SEQ ID NO: 39 and SEQ ID NO: 40. Thermocycler conditions were as follows: 1 cycle at 94° C. for 2 minutes and 30 seconds, 35 cycles at 94° C. for 10 minutes, 65° C. for 20 seconds, 72° C. for 30 seconds, 1 cycle at 72° C. for 7 minutes, followed by a 4° C. hold. The library was deconvoluted down to a positive pool of 1000 clones. E. coli DH10B cells (Gibco BRL) were transformed with this pool by electroporation following manufacturer's protocol. The transformed culture was titered and arrayed out to 96 wells at about 30 cells/well. The cells were grown up in Lbamp overnight at 37° C. An aliquot of the cells were pelleted and PCR was used to identify a positive pool. Thermocycler conditions were as described above. The remaining cells from a positive pool were plated and colonies screened by PCR to identify a positive clone. The clone was sequenced and contained full length zalpha34 [our final zalpha34 nucleotide sequence].

EXAMPLE 3

Zalpha34 Northern and Cloning Protocols

Northern blot analysis was performed using Human Multiple Tissue Blots (MTN1, MTN2 and MTN3) from Clontech (Palo Alto, Calif.) to determine the tissue distribution of human zalpha34. A 159 bp cDNA was obtained by PCR using oligonucleotides SEQ ID NO:39 and SEQ ID NO:40. Thermocycler conditions were as follows: 1 cycle at 94° C. for 2 minutes 30 seconds, 30 cycles at 94° C. for 10 minutes, 65° C. for 20 minutes, 72° C. for 30 minutes, 1 cycle at 72° C. for 7 minutes, followed by a 4° hold. Marathon cDNA (reagents and protocol, Clonetech) from human testis was used as a template. The cDNA was purified using a Gel Extraction Kit (Qiagen, Chatsworth, Calif.) according to manufacturer's instructions. The probe was radioactively labeled using a Rediprime II DNA labeling kit (Amersham, Arlington Heights, Ill.) according to the manufacturer's specifications. The probe was purified using a NUCTRAP push column (Stratagene Cloning Systems, La Jolla, Calif.). The final hybridization solution contained 8 mls ExpressHyb solution (Clontech, Palo Alto, Calif.), 80 µl sheared salmon sperm DNA (10 mg/ml; 5 Prime- 3 Prime, Boulder. Colo.), 48 ?1 human Cot-1 DNA (1 mg/ml, Gibco BRL, Gaithersburg, Md.) and $1.5 \times 10^6$ cpm/ml labeled probe. Hybridization took place overnight at 55° C. The blots were then washed in 2×SSC and 0.1% SDS at room temperature, then with 2×SSC and 0.1% SDS at 65° C., followed by a wash in 0.1×SSC and 0.1% SDS at 65° C. The blots were exposed 2 days (Biomax MS, Kodak, Rochester, N.Y.). Three transcript sizes were observed in testis at about 1.4 kb, 2.8 kb, and 8 kb. Fainter bands corresponding to those sizes were observed in brain, placenta, liver and pancreas. An RNA Master Dot Blot (Clontech) that contained RNAs from various tissues that were normalized to 8 housekeeping genes was also probed and hybridized as described above. Expression was strongest in testis with lesser levels in all brain tissues, pancreas, pituitary gland, and placenta.

---

What is claimed is:

1. An educational kit comprised of a container having an isolated polypeptide comprised of an amino acid sequence selected from the group consisting of SEQ ID NOS: 22–38.

2. An aid for teaching protein chemistry comprised of an isolated polypeptide comprised of an amino acid sequence selected from the group consisting of SEQ ID NOS: 22–38.

3. An isolated polypeptide comprised of an amino acid sequence selected from the group consisting of SEQ ID NOS: 22–38.

* * * * *